United States Patent
Ueda et al.

(10) Patent No.: US 6,277,380 B1
(45) Date of Patent: Aug. 21, 2001

(54) MEASLES VIRUS MUTANT ANTIGEN

(75) Inventors: Shigeharu Ueda, Nishinomiya; Michiko Watanabe, Osaka; Hitomi Kawanish, Sakaide, all of (JP)

(73) Assignee: The Research Foundation for Microbial Diseases of Osaka University, Osaka (JP)

( * ) Notice: Subject to any disclaimer, the term of this patent is extended or adjusted under 35 U.S.C. 154(b) by 0 days.

(21) Appl. No.: 09/230,944

(22) PCT Filed: Jun. 4, 1998

(86) PCT No.: PCT/JP98/02481

§ 371 Date: Feb. 4, 1999

§ 102(e) Date: Feb. 4, 1999

(87) PCT Pub. No.: WO98/55627

PCT Pub. Date: Dec. 10, 1998

(30) Foreign Application Priority Data

Jun. 4, 1997 (JP) .................................................. 9-184285

(51) Int. Cl.$^7$ ........................... A61K 39/165; A61K 39/12
(52) U.S. Cl. ..................................... 424/212.1; 424/205.1; 435/235.1; 530/324; 530/350; 536/23.72
(58) Field of Search ..................... 435/235.1; 424/205.1, 424/212.1; 530/324, 350; 536/23.72

(56) References Cited

U.S. PATENT DOCUMENTS 5,700,470   12/1997   Saito et al. .

FOREIGN PATENT DOCUMENTS

540135 A2  *  3/1992  (EP) .
9321325       10/1993  (WO) .

OTHER PUBLICATIONS

"Virus Taxonomy, Sixth Report of the International Committee on Taxonomy of Viruses," Archives of Virology, F. A. Murphy et al. (eds), pp. 268–272, 1995 (Springer–Verlag Wein, NY).

"Vaccines," 2$^{nd}$ eds., Stanley A Plotkin, et al., pp. 238–239, published by W. B. Saunders Company, 1994.

Shigeharu UEDA, Biken Journal, vol. 14, pp. 155–160 (1971).

Radecke et al., EMBO Journal, vol. 14, No. 23, pp. 5773–5784 (1995).

Sutter et al., FEBS Letters 371, pp. 9–12 (1995).

(Japanese Article) "Cell Technology," Saito et al., vol. 13, No. 8, pp. 757–763 (1994).

Isegawa et al., Molecular and Cellular Probes, vol. 6, pp. 467–475 (1992).

Chirgwin et al., Biochemistry, vol. 18, No. 24, pp. 5294–5299 (1979).

Cattaneo et al., Virology, vol. 173, No. 2, pp. 415–425 (1989).

Rota et al., Virus Research 31, pp. 317–330 (1994).

* cited by examiner

*Primary Examiner*—Ali R. Salimi
(74) *Attorney, Agent, or Firm*—Birch, Stewart, Kolasch & Birch, LLP

(57) ABSTRACT

Disclosed is a measles virus mutant antigen consisting essentially of a measles virus mutant H protein antigen, wherein said measles virus mutant H protein antigen is at least one member selected from the group consisting of the following amino acid sequences (a) to (c): (a) an amino acid sequence of SEQ ID NO: 10; (b) an amino acid sequence of SEQ ID NO: 3 or SEQ ID NO: 11; and (c) an amino acid sequence of SEQ ID NO. 4 or SEQ ID NO: 12 By the use of the measles virus mutant antigen of the present invention, it has become possible to provide efficiently and economically a live attenuated measles vaccine which is adapted for an epidemic strain of measles virus, and a diagnostic reagent capable of accurately detecting infections with an epidemic strain of measles virus.

3 Claims, No Drawings

SEQUENCE LISTING

```
<160> NUMBER OF SEQ ID NOS: 32

<210> SEQ ID NO 1
<211> LENGTH: 1854
<212> TYPE: DNA
<213> ORGANISM: Measles virus
<220> FEATURE:
<221> NAME/KEY: CDS
<222> LOCATION: (1)..(1851)
<220> FEATURE:
<223> OTHER INFORMATION: Attenuated measles virus CAM-70 strain
<220> FEATURE:
<223> OTHER INFORMATION: any n or Xaa = Unknown

<400> SEQUENCE: 1 atg tca cca caa cga gac cgg ata aat gcc ttc tac aaa gat aac ccc        48
Met Ser Pro Gln Arg Asp Arg Ile Asn Ala Phe Tyr Lys Asp Asn Pro
  1               5                  10                  15 cat ccc aag gga agt agg ata gtc att aac aga gaa cat ctt atg att       96
His Pro Lys Gly Ser Arg Ile Val Ile Asn Arg Glu His Leu Met Ile
             20                  25                  30 gat aga cct tat gtt ttg ctg gct gtt ctg ttt gtc atg ttt ctg agc      144
Asp Arg Pro Tyr Val Leu Leu Ala Val Leu Phe Val Met Phe Leu Ser
         35                  40                  45 ttg atc ggg ttg cta gcc att gca ggc att aga ctt cat cgg gca gcc      192
Leu Ile Gly Leu Leu Ala Ile Ala Gly Ile Arg Leu His Arg Ala Ala
     50                  55                  60 atc tac acc gca gag atc cat aaa agc ctc agc acc aat cta gat gta      240
Ile Tyr Thr Ala Glu Ile His Lys Ser Leu Ser Thr Asn Leu Asp Val
 65                  70                  75                  80 act aac tca atc gag cat cag gtc aag gac gtg ctg ata cca ctc ttc      288
Thr Asn Ser Ile Glu His Gln Val Lys Asp Val Leu Ile Pro Leu Phe
                 85                  90                  95
```

-continued

```
aaa atc atc ggt gat gaa gtg ggc ctg agg aca cct cag aga ttc act    336
Lys Ile Ile Gly Asp Glu Val Gly Leu Arg Thr Pro Gln Arg Phe Thr
            100                 105                 110 gac cta gtg aaa ttc atc tct gac aag att aaa ttc ctt aat ccg gat    384
Asp Leu Val Lys Phe Ile Ser Asp Lys Ile Lys Phe Leu Asn Pro Asp
                115                 120                 125 agg gag tac gac ttc aga gat ctc act tgg tgt atc aac ccg cca gag    432
Arg Glu Tyr Asp Phe Arg Asp Leu Thr Trp Cys Ile Asn Pro Pro Glu
            130                 135                 140 aga atc aaa ttg gat tat gat caa tac tgt gca gat gcg gct gct gaa    480
Arg Ile Lys Leu Asp Tyr Asp Gln Tyr Cys Ala Asp Ala Ala Ala Glu
145                 150                 155                 160 gag ctc atg aat gca ttg gtg aac tca act cta ctg gag acc aaa aca    528
Glu Leu Met Asn Ala Leu Val Asn Ser Thr Leu Leu Glu Thr Lys Thr
                165                 170                 175 acc aat cag ttc cta gct gtc tca aag gga aac tgc tca ggg ccc act    576
Thr Asn Gln Phe Leu Ala Val Ser Lys Gly Asn Cys Ser Gly Pro Thr
                180                 185                 190 aca atc aga ggt caa ttc tca aac atg tcg ctg tcc ctg tta gac ttg    624
Thr Ile Arg Gly Gln Phe Ser Asn Met Ser Leu Ser Leu Leu Asp Leu
            195                 200                 205 tat tta ggt cga ggt tac aat gtg tca tct ata gtc act atg aca tcc    672
Tyr Leu Gly Arg Gly Tyr Asn Val Ser Ser Ile Val Thr Met Thr Ser
210                 215                 220 cag gga atg tat ggg gga act tac cta gtg gaa aag cct aat ctg agc    720
Gln Gly Met Tyr Gly Gly Thr Tyr Leu Val Glu Lys Pro Asn Leu Ser
225                 230                 235                 240 agc aaa agg tca gag ttg tca caa ctg agc atg tac cga gtg ttt gaa    768
Ser Lys Arg Ser Glu Leu Ser Gln Leu Ser Met Tyr Arg Val Phe Glu
                245                 250                 255 gta ggt gtt atc aga aat ccg ggt ttg ggg gct ccg gtg ttc cat atg    816
Val Gly Val Ile Arg Asn Pro Gly Leu Gly Ala Pro Val Phe His Met
            260                 265                 270 aca aac tat ctt gag caa cca gtc agt aat gat ctc agc aac tgt atg    864
Thr Asn Tyr Leu Glu Gln Pro Val Ser Asn Asp Leu Ser Asn Cys Met
        275                 280                 285 gtg gct ttg ggg gag ctc aaa ctc gca gcc ctt tgt cac ggg gaa gat    912
Val Ala Leu Gly Glu Leu Lys Leu Ala Ala Leu Cys His Gly Glu Asp
290                 295                 300 tct atc aca att ccc tat cag gga tca ggg aaa ggt gtc agc ttc cag    960
Ser Ile Thr Ile Pro Tyr Gln Gly Ser Gly Lys Gly Val Ser Phe Gln
305                 310                 315                 320 ctc gtc aag cta ggt gtc tgg aaa tcc cca acc gac atg caa tcc tgg    1008
Leu Val Lys Leu Gly Val Trp Lys Ser Pro Thr Asp Met Gln Ser Trp
                325                 330                 335 gtc tcc tta tca acg gat gat cca gtg ata gac agg ctt tac ctc tca    1056
Val Ser Leu Ser Thr Asp Asp Pro Val Ile Asp Arg Leu Tyr Leu Ser
            340                 345                 350 tct cac aga ggt gtt atc gct gac aat caa gca aaa tgg gct gtc ccg    1104
Ser His Arg Gly Val Ile Ala Asp Asn Gln Ala Lys Trp Ala Val Pro
        355                 360                 365 aca aca cga aca gat gac aag ttg cga atg gag aca tgc ttc caa cag    1152
Thr Thr Arg Thr Asp Asp Lys Leu Arg Met Glu Thr Cys Phe Gln Gln
370                 375                 380 gcg tgt aag ggt aaa atc caa gca ctc tgc gag aat ccc gag tgg gca    1200
Ala Cys Lys Gly Lys Ile Gln Ala Leu Cys Glu Asn Pro Glu Trp Ala
385                 390                 395                 400 cca ttg aag gat aac agg att cct tca tac ggg gtc ttg tct gtt gat    1248
Pro Leu Lys Asp Asn Arg Ile Pro Ser Tyr Gly Val Leu Ser Val Asp
```

-continued

| | | | | | | | | | | | | | | | |
|---|---|---|---|---|---|---|---|---|---|---|---|---|---|---|---|
| | | | 405 | | | 410 | | | | 415 | | | | | |
| ctg | agt | ctg | aca | gtt | gag | ctt | aaa | atc | aaa | att | gct | tcg | gga | ttc | ggg | 1296 |
| Leu | Ser | Leu | Thr | Val | Glu | Leu | Lys | Ile | Lys | Ile | Ala | Ser | Gly | Phe | Gly |
| | | | 420 | | | | 425 | | | | 430 | | | | |
| cca | ttg | atc | aca | cac | ggt | tca | ggg | atg | gac | cta | tac | aaa | tcc | aac | cac | 1344 |
| Pro | Leu | Ile | Thr | His | Gly | Ser | Gly | Met | Asp | Leu | Tyr | Lys | Ser | Asn | His |
| | | | 435 | | | | | 440 | | | | 445 | | | |
| aac | aat | gtg | tat | tgg | ctg | aat | atc | ccg | cca | atg | aag | aac | cta | gcc | tta | 1392 |
| Asn | Asn | Val | Tyr | Trp | Leu | Asn | Ile | Pro | Pro | Met | Lys | Asn | Leu | Ala | Leu |
| | | 450 | | | | | 455 | | | | 460 | | | | |
| ggt | gta | atc | aac | aca | ttg | gag | tgg | ata | ccg | aga | ttc | aag | gtt | agc | ccc | 1440 |
| Gly | Val | Ile | Asn | Thr | Leu | Glu | Trp | Ile | Pro | Arg | Phe | Lys | Val | Ser | Pro |
| 465 | | | | | 470 | | | | | 475 | | | | | 480 |
| tac | ctc | ttc | act | gtc | cca | att | aag | gaa | gca | ggc | gaa | gac | tgc | cat | gcc | 1488 |
| Tyr | Leu | Phe | Thr | Val | Pro | Ile | Lys | Glu | Ala | Gly | Glu | Asp | Cys | His | Ala |
| | | | | 485 | | | | | 490 | | | | | 495 | |
| cca | aca | tac | cta | cct | gcg | gag | gtg | ggt | ggt | gat | gtc | aaa | ctc | agt | tcc | 1536 |
| Pro | Thr | Tyr | Leu | Pro | Ala | Glu | Val | Gly | Gly | Asp | Val | Lys | Leu | Ser | Ser |
| | | | 500 | | | | 505 | | | | | 510 | | | |
| aat | ctg | gtg | att | cta | cct | ggt | caa | gat | ctc | caa | tat | gtt | ttg | gca | acc | 1584 |
| Asn | Leu | Val | Ile | Leu | Pro | Gly | Gln | Asp | Leu | Gln | Tyr | Val | Leu | Ala | Thr |
| | | 515 | | | | | 520 | | | | | 525 | | | |
| tac | gat | act | tcc | agg | gtt | gaa | cat | gct | gtg | gtt | tat | tac | gtt | tac | agc | 1632 |
| Tyr | Asp | Thr | Ser | Arg | Val | Glu | His | Ala | Val | Val | Tyr | Tyr | Val | Tyr | Ser |
| | 530 | | | | | 535 | | | | | 540 | | | | |
| cca | agc | cgc | tca | ttt | tct | tac | ttt | tat | cct | ttt | agg | ttg | cct | ata | aag | 1680 |
| Pro | Ser | Arg | Ser | Phe | Ser | Tyr | Phe | Tyr | Pro | Phe | Arg | Leu | Pro | Ile | Lys |
| 545 | | | | | 550 | | | | | 555 | | | | | 560 |
| ggg | gtc | ccc | atc | gaa | tta | caa | gtg | gaa | tgc | ttc | aca | tgg | gac | caa | aaa | 1728 |
| Gly | Val | Pro | Ile | Glu | Leu | Gln | Val | Glu | Cys | Phe | Thr | Trp | Asp | Gln | Lys |
| | | | | 565 | | | | | 570 | | | | | 575 | |
| ctc | tgg | tgc | cgt | cac | ttc | tgt | gtg | ctt | gcg | gac | tca | gaa | tct | ggt | gaa | 1776 |
| Leu | Trp | Cys | Arg | His | Phe | Cys | Val | Leu | Ala | Asp | Ser | Glu | Ser | Gly | Glu |
| | | | 580 | | | | | 585 | | | | | 590 | | |
| cat | atc | act | cac | tct | ggg | atg | gtg | ggc | atg | gaa | gtc | agc | tgc | aca | gtc | 1824 |
| His | Ile | Thr | His | Ser | Gly | Met | Val | Gly | Met | Glu | Val | Ser | Cys | Thr | Val |
| | | 595 | | | | | 600 | | | | | 605 | | | |
| acc | cgg | gaa | gat | gga | acc | aat | cgc | aga | tag | | | | | | | 1854 |
| Thr | Arg | Glu | Asp | Gly | Thr | Asn | Arg | Arg |
| | 610 | | | | | 615 |

```
<210> SEQ ID NO 2
<211> LENGTH: 617
<212> TYPE: PRT
<213> ORGANISM: Measles virus
<220> FEATURE:
<223> OTHER INFORMATION: any n or Xaa = Unknown

<400> SEQUENCE: 2
```

Met Ser Pro Gln Arg Asp Arg Ile Asn Ala Phe Tyr Lys Asp Asn Pro
 1               5                  10                  15

His Pro Lys Gly Ser Arg Ile Val Ile Asn Arg Glu His Leu Met

```
Thr Asn Ser Ile Glu His Gln Val Lys Asp Val Leu Ile Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
            115                 120                 125

Arg Glu Tyr Asp Phe Arg Asp Leu Thr Trp Cys Ile Asn Pro Pro Glu
            130                 135                 140

Arg Ile Lys Leu Asp Tyr Asp Gln Tyr Cys Ala Asp Ala Ala Ala Glu
145                 150                 155                 160

Glu Leu Met Asn Ala Leu Val Asn Ser Thr Leu Leu Glu Thr Lys Thr
                165                 170                 175

Thr Asn Gln Phe Leu Ala Val Ser Lys Gly Asn Cys Ser Gly Pro Thr
                180                 185                 190

Thr Ile Arg Gly Gln Phe Ser Asn Met Ser Leu Ser Leu Leu Asp Leu
            195                 200                 205

Tyr Leu Gly Arg Gly Tyr Asn Val Ser Ser Ile Val Thr Met Thr Ser
            210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
            275                 280                 285

Val Ala Leu Gly Glu Leu Lys Leu Ala Ala Leu Cys His Gly Glu Asp
            290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Ser Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
            355                 360                 365

Thr Thr Arg Thr Asp Asp Lys Leu Arg Met Glu Thr Cys Phe Gln Gln
370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
            435                 440                 445

Asn Asn Val Tyr Trp Leu Asn Ile Pro Pro Met Lys Asn Leu Ala Leu
            450                 455                 460

Gly Val Ile Asn Thr Leu Glu Trp Ile Pro Arg Phe Lys Val Ser Pro
465                 470                 475                 480

Tyr Leu Phe Thr Val Pro Ile Lys Glu Ala Gly Glu Asp Cys His Ala
                485                 490                 495

Pro Thr Tyr Leu Pro Ala Glu Val Gly Gly Asp Val Lys Leu Ser Ser
```

-continued

```
                  500                 505                 510
Asn Leu Val Ile Leu Pro Gly Gln Asp Leu Gln Tyr Val Leu Ala Thr
                515                 520                 525

Tyr Asp Thr Ser Arg Val Glu His Ala Val Val Tyr Tyr Val Tyr Ser
    530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Glu
                580                 585                 590

His Ile Thr His Ser Gly Met Val Gly Met Glu Val Ser Cys Thr Val
            595                 600                 605

Thr Arg Glu Asp Gly Thr Asn Arg Arg
        610                 615
```

<210> SEQ ID NO 3
<211> LENGTH: 524
<212> TYPE: PRT
<213> ORGANISM: Measles virus
<220> FEATURE:
<223> OTHER INFORMATION: Attenuated measles virus CAM-70 strain
<220> FEATURE:
<223> OTHER INFORMATION: any n or Xaa = Unknown

<400> SEQUENCE: 3

```
Ile Pro Leu Phe Lys Ile Ile Gly Asp Glu Val Gly Leu Arg Thr Pro
  1               5                  10                  15

Gln Arg Phe Thr Asp Leu Val Lys Phe Ile Ser Asp Lys Ile Lys Phe
                 20                  25                  30

Leu Asn Pro Asp Arg Glu Tyr Asp Phe Arg Asp Leu Thr Trp Cys Ile
             35                  40                  45

Asn Pro Pro Glu Arg Ile Lys Leu Asp Tyr Asp Gln Tyr Cys Ala Asp
         50                  55                  60

Ala Ala Ala Glu Glu Leu Met Asn Ala Leu Val Asn Ser Thr Leu Leu
 65                  70                  75                  80

Glu Thr Lys Thr Thr Asn Gln Phe Leu Ala Val Ser Lys Gly Asn Cys
                 85                  90                  95

Ser Gly Pro Thr Thr Ile Arg Gly Gln Phe Ser Asn Met Ser Leu Ser
                100                 105                 110

Leu Leu Asp Leu Tyr Leu Gly Arg Gly Tyr Asn Val Ser Ser Ile Val
            115                 120                 125

Thr Met Thr Ser Gln Gly Met Tyr Gly Gly Thr Tyr Leu Val Glu Lys
130                 135                 140

Pro Asn Leu Ser Ser Lys Arg Ser Glu Leu Ser Gln Leu Ser Met Tyr
145                 150                 155                 160

Arg Val Phe Glu Val Gly Val Ile Arg Asn Pro Gly Leu Gly Ala Pro
                165                 170                 175

Val Phe His Met Thr Asn Tyr Leu Glu Gln Pro Val Ser Asn Asp Leu
            180                 185                 190

Ser Asn Cys Met Val Ala Leu Gly Glu Leu Lys Leu Ala Ala Leu Cys
        195                 200                 205

His Gly Glu Asp Ser Ile Thr Ile Pro Tyr Gln Gly Ser Gly Lys Gly
    210                 215                 220

Val Ser Phe Gln Leu Val Lys Leu Gly Val Trp Lys Ser Pro Thr Asp
225                 230                 235                 240
```

```
Met Gln Ser Trp Val Ser Leu Ser Thr Asp Asp Pro Val Ile Asp Arg
                245                 250                 255

Leu Tyr Leu Ser Ser His Arg Gly Val Ile Ala Asp Asn Gln Ala Lys
            260                 265                 270

Trp Ala Val Pro Thr Thr Arg Thr Asp Asp Lys Leu Arg Met Glu Thr
        275                 280                 285

Cys Phe Gln Gln Ala Cys Lys Gly Lys Ile Gln Ala Leu Cys Glu Asn
    290                 295                 300

Pro Glu Trp Ala Pro Leu Lys Asp Asn Arg Ile Pro Ser Tyr Gly Val
305                 310                 315                 320

Leu Ser Val Asp Leu Ser Leu Thr Val Glu Leu Lys Ile Lys Ile Ala
                325                 330                 335

Ser Gly Phe Gly Pro Leu Ile Thr His Gly Ser Gly Met Asp Leu Tyr
            340                 345                 350

Lys Ser Asn His Asn Asn Val Tyr Trp Leu Asn Ile Pro Pro Met Lys
        355                 360                 365

Asn Leu Ala Leu Gly Val Ile Asn Thr Leu Glu Trp Ile Pro Arg Phe
    370                 375                 380

Lys Val Ser Pro Tyr Leu Phe Thr Val Pro Ile Lys Glu Ala Gly Glu
385                 390                 395                 400

Asp Cys His Ala Pro Thr Tyr Leu Pro Ala Glu Val Gly Gly Asp Val
                405                 410                 415

Lys Leu Ser Ser Asn Leu Val Ile Leu Pro Gly Gln Asp Leu Gln Tyr
            420                 425                 430

Val Leu Ala Thr Tyr Asp Thr Ser Arg Val Glu His Ala Val Val Tyr
        435                 440                 445

Tyr Val Tyr Ser Pro Ser Arg Ser Phe Ser Tyr Phe Tyr Pro Phe Arg
    450                 455                 460

Leu Pro Ile Lys Gly Val Pro Ile Glu Leu Gln Val Glu Cys Phe Thr
465                 470                 475                 480

Trp Asp Gln Lys Leu Trp Cys Arg His Phe Cys Val Leu Ala Asp Ser
                485                 490                 495

Glu Ser Gly Glu His Ile Thr His Ser Gly Met Val Gly Met Glu Val
            500                 505                 510

Ser Cys Thr Val Thr Arg Glu Asp Gly Thr Asn Arg
        515                 520

<210> SEQ ID NO 4
<211> LENGTH: 141
<212> TYPE: PRT
<213> ORGANISM: Measles virus
<220> FEATURE:
<223> OTHER INFORMATION: Attenuated measles virus CAM-70 strain
<220> FEATURE:
<223> OTHER INFORMATION: any n or Xaa = Unknown

<400> SEQUENCE: 4

Thr Thr Asn Gln Phe Leu Ala Val Ser Lys Gly Asn Cys Ser Gly Pro
  1               5                  10                  15

Thr Thr Ile Arg Gly Gln Phe Ser Asn Met Ser Leu Ser Leu Leu Asp
            20                  25                  30

Leu Tyr Leu Gly Arg Gly Tyr Asn Val Ser Ser Ile Val Thr Met Thr
        35                  40                  45

Ser Gln Gly Met Tyr Gly Gly Thr Tyr Leu Val Glu Lys Pro Asn Leu
    50                  55                  60
```

-continued

```
Ser Ser Lys Arg Ser Glu Leu Ser Gln Leu Ser Met Tyr Arg Val Phe
 65                  70                  75                  80

Glu Val Gly Val Ile Arg Asn Pro Gly Leu Gly Ala Pro Val Phe His
                 85                  90                  95

Met Thr Asn Tyr Leu Glu Gln Pro Val Ser Asn Asp Leu Ser Asn Cys
            100                 105                 110

Met Val Ala Leu Gly Glu Leu Lys Leu Ala Ala Leu Cys His Gly Glu
        115                 120                 125

Asp Ser Ile Thr Ile Pro Tyr Gln Gly Ser Gly Lys Gly
    130                 135                 140

<210> SEQ ID NO 5
<211> LENGTH: 7
<212> TYPE: PRT
<213> ORGANISM: Measles virus
<220> FEATURE:
<223> OTHER INFORMATION: Attenuated measles virus CAM-70 strain

<400> SEQUENCE: 5

Leu Glu Thr Lys Thr Thr Asn
  1               5

<210> SEQ ID NO 6
<211> LENGTH: 7
<212> TYPE: PRT
<213> ORGANISM: Measles virus
<220> FEATURE:
<223> OTHER INFORMATION: Attenuated measles virus CAM-70 strain

<400> SEQUENCE: 6

Asn Leu Ser Ser Lys Arg Ser
  1               5

<210> SEQ ID NO 7
<211> LENGTH: 6
<212> TYPE: PRT
<213> ORGANISM: Measles virus
<220> FEATURE:
<223> OTHER INFORMATION: Attenuated measles virus CAM -70 strain

<400> SEQUENCE: 7

Glu Gln Pro Val Ser Asn
  1               5

<210> SEQ ID NO 8
<211> LENGTH: 7
<212> TYPE: PRT
<213> ORGANISM: Measles virus
<220> FEATURE:
<223> OTHER INFORMATION: Attenuated measles virus CAM -70 strain

<400> SEQUENCE: 8

His Gly Glu Asp Ser Ile Thr
  1               5

<210> SEQ ID NO 9
<211> LENGTH: 1854
<212> TYPE: DNA
<213> ORGANISM: Measles virus
<220> FEATURE:
<221> NAME/KEY: CDS
<222> LOCATION: (1)..(1851)
<220> FEATURE:
<223> OTHER INFORMATION: Attenuated measles virus NA strain
<220> FEATURE:
<223> OTHER INFORMATION: any n or Xaa = Unknown

```
<400> SEQUENCE: 9 atg tca cca caa cga gac cga ata aat gcc ttc tac aaa gac aac ccc      48
Met Ser Pro Gln Arg Asp Arg Ile Asn Ala Phe Tyr Lys Asp Asn Pro
  1               5                  10                  15 cat cct aag gga agt agg ata gtt att aac aga gaa cat ctt atg att      96
His Pro Lys Gly Ser Arg Ile Val Ile Asn Arg Glu His Leu Met Ile
             20                  25                  30 gat aga cct tat gtt ttg ctg gct gtt cta ttc gtc atg ttt ctg agc     144
Asp Arg Pro Tyr Val Leu Leu Ala Val Leu Phe Val Met Phe Leu Ser
         35                  40                  45 ttg atc ggg ttg cta gcc att gca ggc att aga ctt cat cgg gca gcc     192
Leu Ile Gly Leu Leu Ala Ile Ala Gly Ile Arg Leu His Arg Ala Ala
     50                  55                  60 atc tac act gca gag atc cat aaa agc ctc agc acc aat cta gat gta     240
Ile Tyr Thr Ala Glu Ile His Lys Ser Leu Ser Thr Asn Leu Asp Val
 65                  70                  75                  80 act aac tca atc gag cat cag gtc aag gac gtg ctg aca cca ctc ttc     288
Thr Asn Ser Ile Glu His Gln Val Lys Asp Val Leu Thr Pro Leu Phe
                 85                  90                  95 aag atc atc ggt gat gaa gtg ggc ctg agg aca cct cag aga ttc act     336
Lys Ile Ile Gly Asp Glu Val Gly Leu Arg Thr Pro Gln Arg Phe Thr
            100                 105                 110 gac cta gtg aaa ttc atc tct gac aag att aaa ttc ctt aat ccg gat     384
Asp Leu Val Lys Phe Ile Ser Asp Lys Ile Lys Phe Leu Asn Pro Asp
        115                 120                 125 agg gag tac gac ttc agg gat ctc act tgg tgt atc aac ccg cca gag     432
Arg Glu Tyr Asp Phe Arg Asp Leu Thr Trp Cys Ile Asn Pro Pro Glu
    130                 135                 140 aga atc aaa ttg gat tat gat caa tac tgt gca gat gtg gct gct gaa     480
Arg Ile Lys Leu Asp Tyr Asp Gln Tyr Cys Ala Asp Val Ala Ala Glu
145                 150                 155                 160 gaa ctc atg aat gca ttg gtg aac gca act cta ctg gag gcc agg gca     528
Glu Leu Met Asn Ala Leu Val Asn Ala Thr Leu Leu Glu Ala Arg Ala
                165                 170                 175 acc aat cag ttc cta gct gtc tca aag gga aac tgc tca ggg ccc act     576
Thr Asn Gln Phe Leu Ala Val Ser Lys Gly Asn Cys Ser Gly Pro Thr
            180                 185                 190 aca atc aga ggt caa ttc tca aac atg tcg ctg tcc ctg ttg gac ttg     624
Thr Ile Arg Gly Gln Phe Ser Asn Met Ser Leu Ser Leu Leu Asp Leu
        195                 200                 205 tac tta agt cga ggt tac aat gtg tca tct ata gtc act atg aca tcc     672
Tyr Leu Ser Arg Gly Tyr Asn Val Ser Ser Ile Val Thr Met Thr Ser
    210                 215                 220 cag gga atg tac ggg gga act tac cta gtg gaa aag cct aat ctg agc     720
Gln Gly Met Tyr Gly Gly Thr Tyr Leu Val Glu Lys Pro Asn Leu Ser
225                 230                 235                 240 agt aaa ggg tca gag ttg tca caa ctg agc atg cac cga gtg ttt gaa     768
Ser Lys Gly Ser Glu Leu Ser Gln Leu Ser Met His Arg Val Phe Glu
                245                 250                 255 gta ggt gtg atc aga aat ccg ggt ttg ggg gct ccg gtg ttc cat atg     816
Val Gly Val Ile Arg Asn Pro Gly Leu Gly Ala Pro Val Phe His Met
            260                 265                 270 acg aac tat ttt gag caa tca gtc agt aat gat ttc aac aac tgc atg     864
Thr Asn Tyr Phe Glu Gln Ser Val Ser Asn Asp Phe Asn Asn Cys Met
        275                 280                 285 gtg gct ttg ggg gag ctc aaa ttc gca gcc ctc tgt cac agg gaa gat     912
Val Ala Leu Gly Glu Leu Lys Phe Ala Ala Leu Cys His Arg Glu Asp
    290                 295                 300
```

```
tct atc aca att ccc tat cag ggg tca ggg aaa ggt gtc agc ttc cag         960
Ser Ile Thr Ile Pro Tyr Gln Gly Ser Gly Lys Gly Val Ser Phe Gln
305                 310                 315                 320 ctc gtc aag cta ggt gtc tgg aaa tcc cca acc gac atg caa tcc tgg        1008
Leu Val Lys Leu Gly Val Trp Lys Ser Pro Thr Asp Met Gln Ser Trp
            325                 330                 335 gtc ccc cta tca acg gat gat cca gtg ata gat agg ctt tac ctc tca        1056
Val Pro Leu Ser Thr Asp Asp Pro Val Ile Asp Arg Leu Tyr Leu Ser
        340                 345                 350 tct cac aga ggt gtt atc gct gac aat caa gca aaa tgg gct gtc ccg        1104
Ser His Arg Gly Val Ile Ala Asp Asn Gln Ala Lys Trp Ala Val Pro
    355                 360                 365 aca aca cga aca gat gac aag ttg cga atg gag aca tgc ttc cag cag        1152
Thr Thr Arg Thr Asp Asp Lys Leu Arg Met Glu Thr Cys Phe Gln Gln
370                 375                 380 gcg tgt cag ggc aaa atc caa gca ctc tgc gag aat ccc gag tgg gca        1200
Ala Cys Gln Gly Lys Ile Gln Ala Leu Cys Glu Asn Pro Glu Trp Ala
385                 390                 395                 400 cca ctg aag gac aac agg att cct tca tac ggg gtc ttg tct gtt aat        1248
Pro Leu Lys Asp Asn Arg Ile Pro Ser Tyr Gly Val Leu Ser Val Asn
            405                 410                 415 ctg agt ctg aca gtt gag ctc aaa atc aaa att gct tca gga ttc ggg        1296
Leu Ser Leu Thr Val Glu Leu Lys Ile Lys Ile Ala Ser Gly Phe Gly
        420                 425                 430 cca ttg atc aca cac ggt tca ggg atg gac cta tac aaa tcc aac cac        1344
Pro Leu Ile Thr His Gly Ser Gly Met Asp Leu Tyr Lys Ser Asn His
    435                 440                 445 aac aat gtg tat tgg ctg acc atc ccg cca atg aag aac cta gcc tta        1392
Asn Asn Val Tyr Trp Leu Thr Ile Pro Pro Met Lys Asn Leu Ala Leu
450                 455                 460 ggt gta atc aac aca tta gag tgg ata ccg aga ttc aag gtt agt ccc        1440
Gly Val Ile Asn Thr Leu Glu Trp Ile Pro Arg Phe Lys Val Ser Pro
465                 470                 475                 480 aac ctc ttc act gtt cca atc aag gaa gca ggc gag gac tgc cat gcc        1488
Asn Leu Phe Thr Val Pro Ile Lys Glu Ala Gly Glu Asp Cys His Ala
            485                 490                 495 cca aca tac ctg cct gcg gag gtg gat ggt gat gtc aaa ctc agt tcc        1536
Pro Thr Tyr Leu Pro Ala Glu Val Asp Gly Asp Val Lys Leu Ser Ser
        500                 505                 510 aat ctg gtg att cta cct ggt caa gat ctc caa tat gtt ttg gca acc        1584
Asn Leu Val Ile Leu Pro Gly Gln Asp Leu Gln Tyr Val Leu Ala Thr
    515                 520                 525 tac gat act tcc agg gtt gaa cat gct gtg gtt tat tat gtt tac agc        1632
Tyr Asp Thr Ser Arg Val Glu His Ala Val Val Tyr Tyr Val Tyr Ser
530                 535                 540 ccg agc cgc tca ttt tct tac ttt tat ccc ttt agg ttg cct ata aag        1680
Pro Ser Arg Ser Phe Ser Tyr Phe Tyr Pro Phe Arg Leu Pro Ile Lys
545                 550                 555                 560 ggg gtc ccc atc gaa tta caa gtg gaa tgc ttc aca tgg gac caa aaa        1728
Gly Val Pro Ile Glu Leu Gln Val Glu Cys Phe Thr Trp Asp Gln Lys
            565                 570                 575 ctc tgg tgc cgt cac ttc tgt gtg ctt gcg gac tca gaa tct ggt gga        1776
Leu Trp Cys Arg His Phe Cys Val Leu Ala Asp Ser Glu Ser Gly Gly
        580                 585                 590 cat atc act cac tct gga atg gtg ggc atg gga gtc agc tgc aca gtc        1824
His Ile Thr His Ser Gly Met Val Gly Met Gly Val Ser Cys Thr Val
    595                 600                 605 act cgg gaa gat gga acc aat agc aga tag                                1854
Thr Arg Glu Asp Gly Thr Asn Ser Arg
        610                 615
```

```
<210> SEQ ID NO 10
<211> LENGTH: 617
<212> TYPE: PRT
<213> ORGANISM: Measles virus
<220> FEATURE:
<223> OTHER INFORMATION: any n or Xaa = Unknown

<400> SEQUENCE: 10

Met Ser Pro Gln Arg Asp Arg Ile Asn Ala Phe Tyr Lys Asp Asn Pro
  1               5                  10                  15

His Pro Lys Gly Ser Arg Ile Val Ile Asn Arg Glu His Leu Met Ile
             20                  25                  30

Asp Arg Pro Tyr Val Leu Leu Ala Val Leu Phe Val Met Phe Leu Ser
         35                  40                  45

Leu Ile Gly Leu Leu Ala Ile Ala Gly Ile Arg Leu His Arg Ala Ala
     50                  55                  60

Ile Tyr Thr Ala Glu Ile His Lys Ser Leu Ser Thr Asn Leu Asp Val
 65                  70                  75                  80

Thr Asn Ser Ile Glu His Gln Val Lys Asp Val Leu Thr Pro Leu Phe
                 85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ala Thr Leu Leu Glu Ala Arg Ala
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Ser Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Gly Ser Glu Leu Ser Gln Leu Ser Met His Arg Val Phe Glu
                245                 250                 255

Val Gly Val Ile Arg Asn Pro Gly Leu Gly Ala Pro Val Phe His Met
            260                 265                 270

Thr Asn Tyr Phe Glu Gln Ser Val Ser Asn Asp Phe Asn Asn Cys Met
        275                 280                 285

Val Ala Leu Gly Glu Leu Lys Phe Ala Ala Leu Cys His Arg Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365
```

```
Thr Thr Arg Thr Asp Asp Lys Leu Arg Met Glu Thr Cys Phe Gln Gln
    370                 375                 380

Ala Cys Gln Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asn
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
        435                 440                 445

Asn Asn Val Tyr Trp Leu Thr Ile Pro Pro Met Lys Asn Leu Ala Leu
450                 455                 460

Gly Val Ile Asn Thr Leu Glu Trp Ile Pro Arg Phe Lys Val Ser Pro
465                 470                 475                 480

Asn Leu Phe Thr Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
        515                 520                 525

Tyr Asp Thr Ser Arg Val Glu His Ala Val Val Tyr Tyr Val Tyr Ser
    530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
        595                 600                 605

Thr Arg Glu Asp Gly Thr Asn Ser Arg
    610                 615

<210> SEQ ID NO 11
<211> LENGTH: 524
<212> TYPE: PRT
<213> ORGANISM: Measles virus
<220> FEATURE:
<223> OTHER INFORMATION: Attenuated measles virus NA strain
<220> FEATURE:
<223> OTHER INFORMATION: any n or Xaa = Unknown

<400> SEQUENCE: 11

Thr Pro Leu Phe Lys Ile Ile Gly Asp Glu Val Gly Leu Arg Thr Pro
1               5                   10                  15

Gln Arg Phe Thr Asp Leu Val Lys Phe Ile Ser Asp Lys Ile Lys Phe
            20                  25                  30

Leu Asn Pro Asp Arg Glu Tyr Asp Phe Arg Asp Leu Thr Trp Cys Ile
        35                  40                  45

Asn Pro Pro Glu Arg Ile Lys Leu Asp Tyr Asp Gln Tyr Cys Ala Asp
    50                  55                  60

Val Ala Ala Glu Glu Leu Met Asn Ala Leu Val Asn Ala Thr Leu Leu
65                  70                  75                  80

Glu Ala Arg Ala Thr Asn Gln Phe Leu Ala Val Ser Lys Gly Asn Cys
                85                  90                  95
```

-continued

```
Ser Gly Pro Thr Thr Ile Arg Gly Gln Phe Ser Asn Met Ser Leu Ser
            100                 105                 110
Leu Leu Asp Leu Tyr Leu Ser Arg Gly Tyr Asn Val Ser Ser Ile Val
            115                 120                 125
Thr Met Thr Ser Gln Gly Met Tyr Gly Gly Thr Tyr Leu Val Glu Lys
            130                 135                 140
Pro Asn Leu Ser Ser Lys Gly Ser Glu Leu Ser Gln Leu Ser Met His
145                 150                 155                 160
Arg Val Phe Glu Val Gly Val Ile Arg Asn Pro Gly Leu Gly Ala Pro
                165                 170                 175
Val Phe His Met Thr Asn Tyr Phe Glu Gln Ser Val Ser Asn Asp Phe
                180                 185                 190
Asn Asn Cys Met Val Ala Leu Gly Glu Leu Lys Phe Ala Ala Leu Cys
            195                 200                 205
His Arg Glu Asp Ser Ile Thr Ile Pro Tyr Gln Gly Ser Gly Lys Gly
            210                 215                 220
Val Ser Phe Gln Leu Val Lys Leu Gly Val Trp Lys Ser Pro Thr Asp
225                 230                 235                 240
Met Gln Ser Trp Val Pro Leu Ser Thr Asp Asp Pro Val Ile Asp Arg
                245                 250                 255
Leu Tyr Leu Ser Ser His Arg Gly Val Ile Ala Asp Asn Gln Ala Lys
            260                 265                 270
Trp Ala Val Pro Thr Thr Arg Thr Asp Asp Lys Leu Arg Met Glu Thr
            275                 280                 285
Cys Phe Gln Gln Ala Cys Gln Gly Lys Ile Gln Ala Leu Cys Glu Asn
            290                 295                 300
Pro Glu Trp Ala Pro Leu Lys Asp Asn Arg Ile Pro Ser Tyr Gly Val
305                 310                 315                 320
Leu Ser Val Asn Leu Ser Leu Thr Val Glu Leu Lys Ile Lys Ile Ala
                325                 330                 335
Ser Gly Phe Gly Pro Leu Ile Thr His Gly Ser Gly Met Asp Leu Tyr
            340                 345                 350
Lys Ser Asn His Asn Asn Val Tyr Trp Leu Thr Ile Pro Pro Met Lys
            355                 360                 365
Asn Leu Ala Leu Gly Val Ile Asn Thr Leu Glu Trp Ile Pro Arg Phe
            370                 375                 380
Lys Val Ser Pro Asn Leu Phe Thr Val Pro Ile Lys Glu Ala Gly Glu
385                 390                 395                 400
Asp Cys His Ala Pro Thr Tyr Leu Pro Ala Glu Val Asp Gly Asp Val
                405                 410                 415
Lys Leu Ser Ser Asn Leu Val Ile Leu Pro Gly Gln Asp Leu Gln Tyr
                420                 425                 430
Val Leu Ala Thr Tyr Asp Thr Ser Arg Val Glu His Ala Val Val Tyr
            435                 440                 445
Tyr Val Tyr Ser Pro Ser Arg Ser Phe Ser Tyr Phe Tyr Pro Phe Arg
            450                 455                 460
Leu Pro Ile Lys Gly Val Pro Ile Glu Leu Gln Val Glu Cys Phe Thr
465                 470                 475                 480
Trp Asp Gln Lys Leu Trp Cys Arg His Phe Cys Val Leu Ala Asp Ser
                485                 490                 495
Glu Ser Gly Gly His Ile Thr Ser Gly Met Val Gly Met Gly Val
            500                 505                 510
Ser Cys Thr Val Thr Arg Glu Asp Gly Thr Asn Ser
```

```
<210> SEQ ID NO 12
<211> LENGTH: 141
<212> TYPE: PRT
<213> ORGANISM: Measles virus
<220> FEATURE:
<223> OTHER INFORMATION: Attenuated measles virus NA strain
<220> FEATURE:
<223> OTHER INFORMATION: any n or Xaa = Unknown

<400> SEQUENCE: 12

Ala Thr Asn Gln Phe Leu Ala Val Ser Lys Gly Asn Cys Ser Gly Pro
 1               5                  10                  15

Thr Thr Ile Arg Gly Gln Phe Ser Asn Met Ser Leu Ser Leu Leu Asp
            20                  25                  30

Leu Tyr Leu Ser Arg Gly Tyr Asn Val Ser Ser Ile Val Thr Met Thr
        35                  40                  45

Ser Gln Gly Met Tyr Gly Gly Thr Tyr Leu Val Glu Lys Pro Asn Leu
    50                  55                  60

Ser Ser Lys Gly Ser Glu Leu Ser Gln Leu Ser Met His Arg Val Phe
65                  70                  75                  80

Glu Val Gly Val Ile Arg Asn Pro Gly Leu Gly Ala Pro Val Phe His
                85                  90                  95

Met Thr Asn Tyr Phe Glu Gln Ser Val Ser Asn Asp Phe Asn Asn Cys
            100                 105                 110

Met Val Ala Leu Gly Glu Leu Lys Phe Ala Ala Leu Cys His Arg Glu
        115                 120                 125

Asp Ser Ile Thr Ile Pro Tyr Gln Gly Ser Gly Lys Gly
    130                 135                 140

<210> SEQ ID NO 13
<211> LENGTH: 7
<212> TYPE: PRT
<213> ORGANISM: Measles virus
<220> FEATURE:
<223> OTHER INFORMATION: Attenuated measles virus NA strain

<400> SEQUENCE: 13

Leu Glu Ala Arg Ala Thr Asn
 1               5

<210> SEQ ID NO 14
<211> LENGTH: 7
<212> TYPE: PRT
<213> ORGANISM: Measles virus
<220> FEATURE:
<223> OTHER INFORMATION: Attenuated measles virus NA strain

<400> SEQUENCE: 14

Asn Leu Ser Ser Lys Gly Ser
 1               5

<210> SEQ ID NO 15
<211> LENGTH: 6
<212> TYPE: PRT
<213> ORGANISM: Measles virus
<220> FEATURE:
<223> OTHER INFORMATION: Attenuated measles virus NA strain

<400> SEQUENCE: 15

Glu Gln Ser Val Ser Asn
 1               5
```

```
<210> SEQ ID NO 16
<211> LENGTH: 7
<212> TYPE: PRT
<213> ORGANISM: Measles virus
<220> FEATURE:
<223> OTHER INFORMATION: Attenuated measles virus NA strain

<400> SEQUENCE: 16

His Arg Glu Asp Ser Ile Thr
  1               5

<210> SEQ ID NO 17
<211> LENGTH: 1653
<212> TYPE: DNA
<213> ORGANISM: Measles virus
<220> FEATURE:
<221> NAME/KEY: CDS
<222> LOCATION: (1)..(1650)
<220> FEATURE:
<223> OTHER INFORMATION: Attenuated measles virus CAM-70 strain
<220> FEATURE:
<223> OTHER INFORMATION: any n or Xaa = Unknown

<400> SEQUENCE: 17 atg ggt ctc aag gtg aac gtc tct gcc ata ttc atg gca gta ctg tta        48
Met Gly Leu Lys Val Asn Val Ser Ala Ile Phe Met Ala Val Leu Leu
  1               5                  10                  15 act ctc caa aca ccc acc ggt caa atc cat tgg ggc aat ctc tct aag        96
Thr Leu Gln Thr Pro Thr Gly Gln Ile His Trp Gly Asn Leu Ser Lys
             20                  25                  30 ata ggg gtg gta gga ata gga agt gca agc tac aaa gtt atg act cgt       144
Ile Gly Val Val Gly Ile Gly Ser Ala Ser Tyr Lys Val Met Thr Arg
         35                  40                  45 tcc agc cat cac tca tta gtc ata aaa tta atg ccc aat ata act ctc       192
Ser Ser His His Ser Leu Val Ile Lys Leu Met Pro Asn Ile Thr Leu
     50                  55                  60 ctc aat aac tgc acg agg gta gag att gca gaa tac agg aga cta ctg       240
Leu Asn Asn Cys Thr Arg Val Glu Ile Ala Glu Tyr Arg Arg Leu Leu
 65                  70                  75                  80 aga aca gtt ttg gaa cca att aga gat gca ctt aat gca atg acc cag       288
Arg Thr Val Leu Glu Pro Ile Arg Asp Ala Leu Asn Ala Met Thr Gln
                 85                  90                  95 aat ata aga ccg gtt cag agt gta gct tca ggt agg aga cac aag aga       336
Asn Ile Arg Pro Val Gln Ser Val Ala Ser Gly Arg Arg His Lys Arg
            100                 105                 110 ttt gcg gga gta gtc ctg gca ggt gcg gcc cta ggc gtt gcc aca gct       384
Phe Ala Gly Val Val Leu Ala Gly Ala Ala Leu Gly Val Ala Thr Ala
        115                 120                 125 gct cag ata aca gcc ggc att gca ctt cac cag tcc atg ctg aac tct       432
Ala Gln Ile Thr Ala Gly Ile Ala Leu His Gln Ser Met Leu Asn Ser
    130                 135                 140 caa gcc atc gac aat ctg aga gcg agc ctg gaa act act aat cag gca       480
Gln Ala Ile Asp Asn Leu Arg Ala Ser Leu Glu Thr Thr Asn Gln Ala
145                 150                 155                 160 att gag gca atc gga caa gca ggg cag gag atg ata ttg gct gtt cag       528
Ile Glu Ala Ile Gly Gln Ala Gly Gln Glu Met Ile Leu Ala Val Gln
                165                 170                 175 ggt gtc caa gac tac atc aat aat gag ctg ata ccg tct atg aac caa       576
Gly Val Gln Asp Tyr Ile Asn Asn Glu Leu Ile Pro Ser Met Asn Gln
            180                 185                 190 cta tct tgt gat tta atc ggc cag aag ctc ggg ctc aaa ttg ctc aga       624
Leu Ser Cys Asp Leu Ile Gly Gln Lys Leu Gly Leu Lys Leu Leu Arg
```

```
                195                 200                 205
tac tat aca gaa atc ctg tcg tta ttt ggc ccc agc tta cgg gac ccc      672
Tyr Tyr Thr Glu Ile Leu Ser Leu Phe Gly Pro Ser Leu Arg Asp Pro
    210                 215                 220 ata tct gcg gag ata tct atc cag gct ttg agc tat gcg ctt gga gga      720
Ile Ser Ala Glu Ile Ser Ile Gln Ala Leu Ser Tyr Ala Leu Gly Gly
225                 230                 235                 240 gac atc aat aag gtg tta gaa aag ctc gga tac agt gga ggt gat tta      768
Asp Ile Asn Lys Val Leu Glu Lys Leu Gly Tyr Ser Gly Gly Asp Leu
                245                 250                 255 ctg ggc atc tta gag agc aga gga ata aag gcc cgg ata act cac gtc      816
Leu Gly Ile Leu Glu Ser Arg Gly Ile Lys Ala Arg Ile Thr His Val
            260                 265                 270 gac aca gag tcc tac ttc att gtc ctc agt ata gcc tat ccg acg ctg      864
Asp Thr Glu Ser Tyr Phe Ile Val Leu Ser Ile Ala Tyr Pro Thr Leu
        275                 280                 285 tcc gag att aag ggg gtg att gtc cac cgg cta gag ggg gtc tcg tac      912
Ser Glu Ile Lys Gly Val Ile Val His Arg Leu Glu Gly Val Ser Tyr
    290                 295                 300 aac ata ggc tct caa gag tgg tat acc act gtg ccc aag tat gtt gca      960
Asn Ile Gly Ser Gln Glu Trp Tyr Thr Thr Val Pro Lys Tyr Val Ala
305                 310                 315                 320 acc caa ggg tac ctt atc tcg aat ttt gat gag tca tcg tgt act ttc     1008
Thr Gln Gly Tyr Leu Ile Ser Asn Phe Asp Glu Ser Ser Cys Thr Phe
                325                 330                 335 atg cca gag ggg act gtg tgc agc caa aat gcc ttg tac ccg atg agt     1056
Met Pro Glu Gly Thr Val Cys Ser Gln Asn Ala Leu Tyr Pro Met Ser
            340                 345                 350 cct ctg ctc caa gaa tgc ctc cgg ggg ttc acc aag tcc tgt gct cgt     1104
Pro Leu Leu Gln Glu Cys Leu Arg Gly Phe Thr Lys Ser Cys Ala Arg
        355                 360                 365 aca ctc gta tcc ggg tct ttt ggg aac cgg ttc att tta tca caa ggg     1152
Thr Leu Val Ser Gly Ser Phe Gly Asn Arg Phe Ile Leu Ser Gln Gly
    370                 375                 380 aac cta ata gcc aat tgt gca tca atc ctt tgc aag tgt cac aca aca     1200
Asn Leu Ile Ala Asn Cys Ala Ser Ile Leu Cys Lys Cys His Thr Thr
385                 390                 395                 400 gga acg atc att aat caa gac cct gac aag atc cta aca tac att gct     1248
Gly Thr Ile Ile Asn Gln Asp Pro Asp Lys Ile Leu Thr Tyr Ile Ala
                405                 410                 415 gac gat cac tgc ccg gta gtc gag gtg aac ggc gtg acc atc caa gtc     1296
Asp Asp His Cys Pro Val Val Glu Val Asn Gly Val Thr Ile Gln Val
            420                 425                 430 ggg agc agg agg tat cca gac gct gtg tac ttg cac aga att gac ctc     1344
Gly Ser Arg Arg Tyr Pro Asp Ala Val Tyr Leu His Arg Ile Asp Leu
        435                 440                 445 ggt cct ccc ata tca ttg gag agg ttg gac gta ggg aca aat ctg ggg     1392
Gly Pro Pro Ile Ser Leu Glu Arg Leu Asp Val Gly Thr Asn Leu Gly
    450                 455                 460 aat gca att gct aag ttg gag gat gcc aag gaa ttg ttg gag tca tcg     1440
Asn Ala Ile Ala Lys Leu Glu Asp Ala Lys Glu Leu Leu Glu Ser Ser
465                 470                 475                 480 gac cag ata ttg agg agt atg aaa ggt tta tcg agc act agc ata gtc     1488
Asp Gln Ile Leu Arg Ser Met Lys Gly Leu Ser Ser Thr Ser Ile Val
                485                 490                 495 tac atc ctg att gca gtg tgt ctt gga ggg ttg ata ggg atc ccc gct     1536
Tyr Ile Leu Ile Ala Val Cys Leu Gly Gly Leu Ile Gly Ile Pro Ala
            500                 505                 510 tta ata tgt tgc tgc agg ggg cgt tgt aac aaa aag gga gaa caa gtt     1584
```

```
Leu Ile Cys Cys Cys Arg Gly Arg Cys Asn Lys Lys Gly Glu Gln Val
            515                 520                 525 ggt atg tca aga cca ggc cta aag cct gat ctt acg gga aca tca aaa          1632
Gly Met Ser Arg Pro Gly Leu Lys Pro Asp Leu Thr Gly Thr Ser Lys
    530                 535                 540 tcc tat gta agg tcg ctc tga                                              1653
Ser Tyr Val Arg Ser Leu
545                 550

<210> SEQ ID NO 18
<211> LENGTH: 550
<212> TYPE: PRT
<213> ORGANISM: Measles virus
<220> FEATURE:
<223> OTHER INFORMATION: any n or Xaa = Unknown

<400> SEQUENCE: 18

Met Gly Leu Lys Val Asn Val Ser Ala Ile Phe Met Ala Val

```
305                 310                 315                 320
Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Phe Thr Lys Ser Cys Ala Arg
        355                 360                 365

Thr Leu Val Ser Gly Ser Phe Gly Asn Arg Phe Ile Leu Ser Gln Gly
    370                 375                 380

Asn Leu Ile Ala Asn Cys Ala Ser Ile Leu Cys Lys Cys His Thr Thr
385                 390                 395                 400

Gly Thr Ile Ile Asn Gln Asp Pro Asp Lys Ile Leu Thr Tyr Ile Ala
                405                 410                 415

Asp Asp His Cys Pro Val Val Glu Val Asn Gly Val Thr Ile Gln Val
            420                 425                 430

Gly Ser Arg Arg Tyr Pro Asp Ala Val Tyr Leu His Arg Ile Asp Leu
        435                 440                 445

Gly Pro Pro Ile Ser Leu Glu Arg Leu Asp Val Gly Thr Asn Leu Gly
    450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Ser Ile Val
                485                 490                 495

Tyr Ile Leu Ile Ala Val Cys Leu Gly Gly Leu Ile Gly Ile Pro Ala
            500                 505                 510

Leu Ile Cys Cys Cys Arg Gly Arg Cys Asn Lys Lys Gly Glu Gln Val
        515                 520                 525

Gly Met Ser Arg Pro Gly Leu Lys Pro Asp Leu Thr Gly Thr Ser Lys
    530                 535                 540

Ser Tyr Val Arg Ser Leu
545                 550

<210> SEQ ID NO 19
<211> LENGTH: 1653
<212> TYPE: DNA
<213> ORGANISM: Measles virus
<220> FEATURE:
<221> NAME/KEY: CDS
<222> LOCATION: (1)..(1650)
<220> FEATURE:
<223> OTHER INFORMATION: Attenuated measles virus NA strain
<220> FEATURE:
<223> OTHER INFORMATION: any n or Xaa = Unknown

<400> SEQUENCE: 19 atg ggt ctc aag gtg aac gtc tct gcc ata ctc atg gca gta ctg tta     48
Met Gly Leu Lys Val Asn Val Ser Ala Ile Leu Met Ala Val Leu Leu
1               5                   10                  15 act ctc caa aca ccc acc ggt caa atc cat tgg ggc aat ctc tct aag     96
Thr Leu Gln Thr Pro Thr Gly Gln Ile His Trp Gly Asn Leu Ser Lys
            20                  25                  30 ata ggg gtg gta ggg ata gga agt gca agc tac aaa gtt atg act cgt    144
Ile Gly Val Val Gly Ile Gly Ser Ala Ser Tyr Lys Val Met Thr Arg
        35                  40                  45 tcc agc cat caa tca ttg gtc ata aaa tta atg ccc aat ata act ctc    192
Ser Ser His Gln Ser Leu Val Ile Lys Leu Met Pro Asn Ile Thr Leu
    50                  55                  60 ctc aat aac tgc acg agg gta gag att gca gaa tac agg aga cta ctg    240
Leu Asn Asn Cys Thr Arg Val Glu Ile Ala Glu Tyr Arg Arg Leu Leu
```

-continued

|    |    | 65 |    |    |    | 70 |    |    |    | 75 |    |    |    | 80 |    |      |
|----|----|----|----|----|----|----|----|----|----|----|----|----|----|----|----|------|
| aga | aca | gtt | ttg | gaa | cca | att | aga | gat | gca | ctt | aat | gca | atg | acc | cag | 288 |
| Arg | Thr | Val | Leu | Glu | Pro | Ile | Arg | Asp | Ala | Leu | Asn | Ala | Met | Thr | Gln |      |
|    |    |    |    |    | 85 |    |    |    |    | 90 |    |    |    |    | 95 |      |

| aat | ata | aga | ccg | gtt | cag | agt | gta | gcc | tca | agt | agg | aga | cac | aag | aga | 336 |
| Asn | Ile | Arg | Pro | Val | Gln | Ser | Val | Ala | Ser | Ser | Arg | Arg | His | Lys | Arg |      |
|     |     |     | 100 |     |     |     |     | 105 |     |     |     |     | 110 |     |     |      |

| ttt | gcg | gga | gtt | gtc | ctg | gca | ggt | gcg | gcc | cta | ggc | gtt | gcc | aca | gct | 384 |
| Phe | Ala | Gly | Val | Val | Leu | Ala | Gly | Ala | Ala | Leu | Gly | Val | Ala | Thr | Ala |      |
|     |     | 115 |     |     |     |     | 120 |     |     |     |     | 125 |     |     |     |      |

| gct | cag | ata | aca | gcc | ggc | att | gca | ctt | cac | cag | tcc | atg | ctg | aac | tct | 432 |
| Ala | Gln | Ile | Thr | Ala | Gly | Ile | Ala | Leu | His | Gln | Ser | Met | Leu | Asn | Ser |      |
|     | 130 |     |     |     |     | 135 |     |     |     |     | 140 |     |     |     |     |      |

| caa | gcc | atc | gac | aat | ctg | aga | gca | agc | ctg | gaa | act | act | aat | cag | gcg | 480 |
| Gln | Ala | Ile | Asp | Asn | Leu | Arg | Ala | Ser | Leu | Glu | Thr | Thr | Asn | Gln | Ala |      |
| 145 |     |     |     |     | 150 |     |     |     |     | 155 |     |     |     |     | 160 |      |

| att | gag | gca | atc | aga | caa | gca | ggg | cag | gag | atg | ata | ttg | gct | gtt | cag | 528 |
| Ile | Glu | Ala | Ile | Arg | Gln | Ala | Gly | Gln | Glu | Met | Ile | Leu | Ala | Val | Gln |      |
|     |     |     |     | 165 |     |     |     |     | 170 |     |     |     |     | 175 |     |      |

| ggt | gtc | caa | gac | tac | atc | aat | aat | gag | ctg | ata | ccg | tct | atg | aac | caa | 576 |
| Gly | Val | Gln | Asp | Tyr | Ile | Asn | Asn | Glu | Leu | Ile | Pro | Ser | Met | Asn | Gln |      |
|     |     |     | 180 |     |     |     |     | 185 |     |     |     |     | 190 |     |     |      |

| cta | tct | tgt | gat | tta | atc | ggc | cag | aag | cta | ggg | ctc | aaa | ttg | ctc | aga | 624 |
| Leu | Ser | Cys | Asp | Leu | Ile | Gly | Gln | Lys | Leu | Gly | Leu | Lys | Leu | Leu | Arg |      |
|     |     | 195 |     |     |     |     | 200 |     |     |     |     | 205 |     |     |     |      |

| tac | tat | aca | gaa | atc | ctg | tca | tta | ttt | ggc | ccc | agc | cta | cgg | gac | ccc | 672 |
| Tyr | Tyr | Thr | Glu | Ile | Leu | Ser | Leu | Phe | Gly | Pro | Ser | Leu | Arg | Asp | Pro |      |
|     | 210 |     |     |     |     | 215 |     |     |     |     | 220 |     |     |     |     |      |

| ata | tct | gcg | gag | ata | tcc | atc | cag | gct | ttg | agc | tat | gcg | ctt | gga | gga | 720 |
| Ile | Ser | Ala | Glu | Ile | Ser | Ile | Gln | Ala | Leu | Ser | Tyr | Ala | Leu | Gly | Gly |      |
| 225 |     |     |     |     | 230 |     |     |     |     | 235 |     |     |     |     | 240 |      |

| gat | atc | aat | aag | gtg | tta | gaa | aag | ctc | gga | tac | agt | gga | ggt | gat | tta | 768 |
| Asp | Ile | Asn | Lys | Val | Leu | Glu | Lys | Leu | Gly | Tyr | Ser | Gly | Gly | Asp | Leu |      |
|     |     |     | 245 |     |     |     |     | 250 |     |     |     |     | 255 |     |     |      |

| ctg | ggc | atc | tta | gag | agc | aga | gga | ata | aag | gcc | cgg | ata | act | cac | gtc | 816 |
| Leu | Gly | Ile | Leu | Glu | Ser | Arg | Gly | Ile | Lys | Ala | Arg | Ile | Thr | His | Val |      |
|     |     |     | 260 |     |     |     |     | 265 |     |     |     |     | 270 |     |     |      |

| gac | aca | gag | tcc | tac | ttc | att | gta | ctc | agt | ata | gcc | tat | ccg | acg | ctg | 864 |
| Asp | Thr | Glu | Ser | Tyr | Phe | Ile | Val | Leu | Ser | Ile | Ala | Tyr | Pro | Thr | Leu |      |
|     | 275 |     |     |     |     | 280 |     |     |     |     | 285 |     |     |     |     |      |

| tcc | gag | att | aag | ggg | gtg | att | gtc | cac | cgg | cta | gag | ggg | gtc | tcg | tac | 912 |
| Ser | Glu | Ile | Lys | Gly | Val | Ile | Val | His | Arg | Leu | Glu | Gly | Val | Ser | Tyr |      |
|     |     | 290 |     |     |     |     | 295 |     |     |     |     | 300 |     |     |     |      |

| aat | ata | ggc | tct | caa | gag | tgg | tat | acc | act | gtg | ccc | aag | tat | gtt | gca | 960 |
| Asn | Ile | Gly | Ser | Gln | Glu | Trp | Tyr | Thr | Thr | Val | Pro | Lys | Tyr | Val | Ala |      |
| 305 |     |     |     |     | 310 |     |     |     |     | 315 |     |     |     |     | 320 |      |

| acc | cag | ggg | tac | ctt | atc | tcg | aat | ttt | gat | gag | tca | tcg | tgt | act | ttc | 1008 |
| Thr | Gln | Gly | Tyr | Leu | Ile | Ser | Asn | Phe | Asp | Glu | Ser | Ser | Cys | Thr | Phe |      |
|     |     |     |     | 325 |     |     |     |     | 330 |     |     |     |     | 335 |     |      |

| atg | cca | gag | ggg | act | gtg | tgc | agc | caa | aat | gcc | ttg | tac | ccg | atg | agt | 1056 |
| Met | Pro | Glu | Gly | Thr | Val | Cys | Ser | Gln | Asn | Ala | Leu | Tyr | Pro | Met | Ser |      |
|     |     |     | 340 |     |     |     |     | 345 |     |     |     |     | 350 |     |     |      |

| cct | ctg | ctc | caa | gaa | tgc | ctc | cgg | ggg | tcc | acc | aag | tcc | tgt | gct | cgt | 1104 |
| Pro | Leu | Leu | Gln | Glu | Cys | Leu | Arg | Gly | Ser | Thr | Lys | Ser | Cys | Ala | Arg |      |
|     |     | 355 |     |     |     |     | 360 |     |     |     |     | 365 |     |     |     |      |

| aca | ctc | gta | tcc | ggg | tct | ttt | ggg | aac | cgg | ttc | att | tta | tca | caa | ggg | 1152 |
| Thr | Leu | Val | Ser | Gly | Ser | Phe | Gly | Asn | Arg | Phe | Ile | Leu | Ser | Gln | Gly |      |
|     | 370 |     |     |     |     | 375 |     |     |     |     | 380 |     |     |     |     |      |

| aac | cta | ata | gcc | aat | tgt | gca | tca | atc | ctc | tgc | aag | tgt | tac | aca | aca | 1200 |

```
                                                                -continued

Asn Leu Ile Ala Asn Cys Ala Ser Ile Leu Cys Lys Cys Tyr Thr Thr
385                 390                 395                 400 gga acg atc att aat caa gac cct gac aag atc cta aca tac att gct      1248
Gly Thr Ile Ile Asn Gln Asp Pro Asp Lys Ile Leu Thr Tyr Ile Ala
                    405                 410                 415 gcc gat cac tgc ccg gtg gtc gag gtg aac ggt gtg acc atc cag gtc      1296
Ala Asp His Cys Pro Val Val Glu Val Asn Gly Val Thr Ile Gln Val
                420                 425                 430 ggg agc agg agg tat ccg gac gca gtg tac ttg cac aga att gac ctc      1344
Gly Ser Arg Arg Tyr Pro Asp Ala Val Tyr Leu His Arg Ile Asp Leu
            435                 440                 445 ggt cct ccc ata tca ttg gag agg ttg gac gtg ggg acg aat ctg ggg      1392
Gly Pro Pro Ile Ser Leu Glu Arg Leu Asp Val Gly Thr Asn Leu Gly
450                 455                 460 aat gca att gct aag ttg gag gat gcc aaa gaa ttg ttg gag tca tcg      1440
Asn Ala Ile Ala Lys Leu Glu Asp Ala Lys Glu Leu Leu Glu Ser Ser
465                 470                 475                 480 gac cag ata ttg agg agt atg aaa ggt tta tcg agc act agc ata gtt      1488
Asp Gln Ile Leu Arg Ser Met Lys Gly Leu Ser Ser Thr Ser Ile Val
                    485                 490                 495 tac atc ctg att gca gtg tgt ctt ggg ggg ttg ata ggg atc ccc gct      1536
Tyr Ile Leu Ile Ala Val Cys Leu Gly Gly Leu Ile Gly Ile Pro Ala
                500                 505                 510 tta ata tgt tgc tgc agg ggg cgt tgt aac aga aag gga gag caa gtt      1584
Leu Ile Cys Cys Cys Arg Gly Arg Cys Asn Arg Lys Gly Glu Gln Val
            515                 520                 525 ggt atg tca aga cca ggc cta aag cct gat ctt aca ggg aca tca aaa      1632
Gly Met Ser Arg Pro Gly Leu Lys Pro Asp Leu Thr Gly Thr Ser Lys
530                 535                 540 tcc tat gta agg tcg ctc tga                                          1653
Ser Tyr Val Arg Ser Leu
545                 550

<210> SEQ ID NO 20
<211> LENGTH: 550
<212> TYPE: PRT
<213> ORGANISM: Measles virus
<220> FEATURE:
<223> OTHER INFORMATION: any n or Xaa = Unknown

<400> SEQUENCE: 20

Met Gly Leu Lys Val Asn Val Ser Ala Ile Leu Met Ala Val Leu Leu
 1               5                  10                  15

Thr Leu Gln Thr Pro Thr Gly Gln Ile His Trp Gly Asn Leu Ser Lys
                20                  25                  30

Ile Gly Val Val Gly Ile Gly Ser Ala Ser Tyr Lys Val Met Thr Arg
            35                  40                  45

Ser Ser His Gln Ser Leu Val Ile Lys Leu Met Pro Asn Ile Thr Leu
        50                  55                  60

Leu Asn Asn Cys Thr Arg Val Glu Ile Ala Glu Tyr Arg Arg Leu Leu
65                  70                  75                  80

Arg Thr Val Leu Glu Pro Ile Arg Asp Ala Leu Asn Ala Met Thr Gln
                85                  90                  95

Asn Ile Arg Pro Val Gln Ser Val Ala Ser Ser Arg Arg His Lys Arg
                100                 105                 110

Phe Ala Gly Val Val Leu Ala Gly Ala Ala Leu Gly Val Ala Thr Ala
            115                 120                 125

Ala Gln Ile Thr Ala Gly Ile Ala Leu His Gln Ser Met Leu Asn Ser
        130                 135                 140
```

```
Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Val Gln
            165                 170                 175

Gly Val Gln Asp Tyr Ile Asn Asn Glu Leu Ile Pro Ser Met Asn Gln
        180                 185                 190

Leu Ser Cys Asp Leu Ile Gly Gln Lys Leu Gly Leu Lys Leu Leu Arg
    195                 200                 205

Tyr Tyr Thr Glu Ile Leu Ser Leu Phe Gly Pro Ser Leu Arg Asp Pro
210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
            245                 250                 255

Leu Gly Ile Leu Glu Ser Arg Gly Ile Lys Ala Arg Ile Thr His Val
        260                 265                 270

Asp Thr Glu Ser Tyr Phe Ile Val Leu Ser Ile Ala Tyr Pro Thr Leu
    275                 280                 285

Ser Glu Ile Lys Gly Val Ile Val His Arg Leu Glu Gly Val Ser Tyr
290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
            325                 330                 335

Met Pro Glu Gly Thr Val Cys Ser Gln Asn Ala Leu Tyr Pro Met Ser
        340                 345                 350

Pro Leu Leu Gln Glu Cys Leu Arg Gly Ser Thr Lys Ser Cys Ala Arg
    355                 360                 365

Thr Leu Val Ser Gly Ser Phe Gly Asn Arg Phe Ile Leu Ser Gln Gly
370                 375                 380

Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
            405                 410                 415

Ala Asp His Cys Pro Val Val Glu Val Asn Gly Val Thr Ile Gln Val
        420                 425                 430

Gly Ser Arg Arg Tyr Pro Asp Ala Val Tyr Leu His Arg Ile Asp Leu
    435                 440                 445

Gly Pro Pro Ile Ser Leu Glu Arg Leu Asp Val Gly Thr Asn Leu Gly
450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Ser Ile Val
            485                 490                 495

Tyr Ile Leu Ile Ala Val Cys Leu Gly Gly Leu Ile Gly Ile Pro Ala
        500                 505                 510

Leu Ile Cys Cys Cys Arg Gly Arg Cys Asn Arg Lys Gly Glu Gln Val
    515                 520                 525

Gly Met Ser Arg Pro Gly Leu Lys Pro Asp Leu Thr Gly Thr Ser Lys
530                 535                 540

Ser Tyr Val Arg Ser Leu
545                 550
```

```
<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:primer F28

<400> SEQUENCE: 21
agaatcaaga ctcatccaat gtc                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:primer CF7

<400> SEQUENCE: 22
ttgagagttc agcatggact ggt                                              23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:primer CF3

<400> SEQUENCE: 23
acaatgaagt aggactctgt gtc                                              23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:primer F3

<400> SEQUENCE: 24
ggaacctaat agccaattgt gca                                              23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:primer CF2

<400> SEQUENCE: 25
cgaggtcaat tctgtgcaag tac                                              23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence:primer F4

<400> SEQUENCE: 26
aaagggagaa caagttggta tgt                                              23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:primer CF1
```

```
<400> SEQUENCE: 27
gatattgttc ggccagaggg aag                                              23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:primer MP5

<400> SEQUENCE: 28
atgtcaccac aacgagaccg gat                                              23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:primer MP4

<400> SEQUENCE: 29
gagattcact gacctagtga aat                                              23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:primer MP2

<400> SEQUENCE: 30
tcgctgtccc tgttagactt gta                                              23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence:primer H8

<400> SEQUENCE: 31
gagcaaccag tcagtaatga tct                                              23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:primer MP3

<400> SEQUENCE: 32
atgcctgatg tctgggtgac atc                                              23
```

MEASLES VIRUS MUTANT ANTIGEN

This application is the national phase under 35 U.S.C. §371 of prior PCT International Application No. PCT/JP98/02481 which has an International filing date of Jun. 4, 1998 which designated the United States of America.

BACKGROUND OF THE INVENTION

1. Field of the Invention

The present invention relates to a measles virus mutant antigen and a gene coding for the same. More particularly, the present invention is concerned with a measles virus mutant antigen comprising at least one protein antigen selected from the group consisting of a measles virus mutant H protein antigen and a measles virus mutant F protein antigen, and a measles virus mutant gene coding for the measles virus mutant antigen. By the use of the measles virus mutant antigen or the gene coding for the same of the present invention, it has become possible to provide efficiently and economically a live attenuated measles vaccine. or gene vaccine which is adapted for an epidemic strain of measles virus, and a diagnostic reagent capable of accurately detecting infections with an epidemic strain of measles virus.

2. Prior Art (1) Pathogenicity: Measles virus is the pathogen of measles, and it is distributed widely throughout the world. This virus is highly infectious, and when a person suffers a droplet infection with a measles virus, damage occurs mainly in the respiratory system and reticuloendothelial tissue, thereby causing an acute disease. A person suffering from measles shows systemic symptoms, such as high fever, catarrh and rash. Further, in severe cases, measles is complicated with bacterial pneumonia, tympanitis and acute encephalitis. In 1996, the number of measles patients and number of deaths due to measles in the world were estimated to be about 42 million and about 1 million 10 thousand, respectively ["The World Health Report 1997", p. 15, WHO (World Health Organization) published in 1997]. As apparent from the above, measles is an infectious disease which should be taken into serious consideration, and eradication of measles by vaccines is desired throughout the world. In this situation, the Expanded Program on Immunization (EPI) of World Health Organization (WHO) has already adopted a measles eradication program with the goal of controlling measles by the year 2010.

(2) Viral morphology and genomic structure: According to the Sixth Report of the International Committee on Taxonomy of Viruses, the measles virus is classified under the order Mononegavirales, family Paramyxoviridae, genus Morbillivirus. The virion of the measles virus is generally spherical (diameter: about 150 nm) and has an envelope composed of a lipid bilayer. On the surface of the envelope are spike-like projections composed of an H (hemagglutinin) protein and composed of an F (fusion) protein, and the bases of the projections (proteins) are supported by a matrix membrane protein at the inner layer of the envelope. The nucleocapsid present in the inside of the envelope consists of measles virus genomic RNA which is a linear, non-segmented (−) sense (that is, mononega) RNA having a length of about 16 kb, and proteins. The genomic RNA codes for N (nucleocapsid-associated proteins), P/C/V (phosphoprotein/C protein/V protein: coded for by tricistronic gene), M (matrix protein), F (fusion protein), H (hemagglutinin protein) and L (large putative polymerase protein), and the coding regions are located in this order from the 3' end to the 5' end of the genome ("Virus Taxonomy: Sixth Report of the International Committee on Taxonomy of Viruses", Archives of Virology, Supplement 10, pp. 268–270 and pp. 271–272, 1995).

(3) Conventional virus strain for live attenuated measles vaccine: Examples of the virus strains known for live attenuated measles vaccine are: CAM-70, Schwarz FF8, AIK-C, AIK-HDC, TD97, Moraten, Connaught, Schwarz, Edmonston B, Edmonston-Zagreb, Leningrad-16, Shanghai-191, Changchum-47 and Beijing (S. A. Plotokin and E. A. Mortimer, "Vaccines", 2nd edition, pp. 238–239, published by W. B. Saunders Company, 1994). These virus strains are either a host-range mutant or a temperature mutant of measles virus which are attenuated to ensure safety and effectiveness so as to be used as an active component for a live vaccine, and such viruses are obtained by sequentially subjecting an isolated strain (wild measles virus) to passages of culture under different conditions prepared by combining various factors, such as host cell, culture temperature, and pH and composition of a culture medium.

(4) Prevention: Vaccines for preventing measles were put to practical use in the early 1960's. At the beginning, the majority of the measles vaccines used was killed (or inactivated) vaccines (abbreviated "K") containing killed measles viruses as an active component of the vaccine. However, the killed measles vaccine had an unsatisfactory immunological effect, and further, it induced serious atypical measles. In this situation, the use of a live vaccine (abbreviated "L") containing live attenuated measles viruses as an active component of the vaccine gradually became predominant in the late 1960's. A combination of K and L vaccines was adopted, but since the 1970's, a further attenuated live vaccine (abbreviated "FL") obtained by further attenuating the above-mentioned live vaccine virus has become commercially available throughout the world for practical use. With respect to the live vaccine, each of the live attenuated measles vaccine strains mentioned in item (3) above is used as an active component of the vaccine.

(5) Problems of measles vaccine and diagnosis: With respect to the maintenance of immunity obtained by using a conventional live attenuated measles virus vaccine, some problems have arisen since the early 1970's. Illustratively stated, reports on secondary vaccine failure and modified measles have been made, in which it is reported that, people who have been vaccinated with measles vaccine were reinfected with measles and suffered from symptoms which are different from that of the natural infection (in general, the symptoms are mild compared to those of the natural infection, but serious in rare cases). Such reports on reinfection in various parts of the world were made sporadically in the latter half of the 1980's, and the reports are frequently made in the 1990's. Therefore, the development of means for preventing the reinfection and for determining the infecting virus has been earnestly desired by not only the people in various countries of the world, but also by the WHO from the viewpoint of the above-mentioned eradication program on measles. However, a measles vaccine or diagnostic reagent effective for preventing the infection with the currently prevailing measles viruses has not yet been realized.

SUMMARY OF THE INVENTION

The inventors of the present invention have not only studied measles from the viewpoint of clinics, epidemiology and vaccine, but also studied various measles viruses, such as vaccine strains, epidemic strains and isolated fresh strains, from the viewpoint of virology and immunology, together with the genetic analyses of these virus strains. In particular, the primary inventor of the present invention has been continuing his studies for more than 30 years. The inventors of the present invention have further made extensive and intensive studies for elucidating the differences in antigenicity or immunogenicity between conventional virulent strains, and virulent mutants including epidemic strains, and also for identifying the causes of such differences. As a result, they have surprisingly found that, with respect to the mutants, the specific regions in each of the genes coding for the H protein and F protein possess mutations which result in amino acid substitutions. Further, the inventors of the present invention have found that the mutated regions in the H protein and F protein are effective as mutant antigens of the measles virus. The present invention has been completed, based on these novel findings.

Therefore, it is an object of the present invention to provide a measles virus mutant antigen, comprising at least one protein antigen selected from the group consisting of a measles virus mutant H protein antigen and a measles virus mutant F protein antigen, which is advantageous for preparing a vaccine and a diagnostic reagent for a virus of epidemic measles.

It is a further object of the present invention to provide a measles virus mutant gene, comprising at least one gene selected from the group consisting of a gene coding for a measles virus mutant H protein antigen and a gene coding for a measles virus mutant F protein antigen, which is advantageous for preparing a gene vaccine and a diagnostic reagent for a virus of epidemic measles.

The foregoing and other objects, features and advantages of the present invention will be apparent to those skilled in the art from the following detailed description and the appended claims taken in connection with the accompanying sequence listing.

BRIEF DESCRIPTION OF THE SEQUENCE LISTING

In each of SEQ ID NOs: 1 to 20, the left end and the right end of the amino acid sequence are the N-terminus and the C-terminus, respectively.

SEQ ID NO: 1 is the nucleotide sequence of the cDNA corresponding to the genomic RNA coding for the H protein of the attenuated measles virus CAM-70 strain and the whole amino acid sequence encoded by the nucleotide sequence;

SEQ ID NO: 2 is the whole amino acid sequence of the H protein of the attenuated measles virus CAM-70 strain;

SEQ ID NO: 3 is the amino acid sequence of the fragmentary peptide consisting of the 93rd to 616th amino acids in SEQ ID NO: 2;

SEQ ID NO: 4 is the amino acid sequence of the fragmentary peptide consisting of the 176th to 316th amino acids in SEQ ID NO: 2;

SEQ ID NO: 5 is the amino acid sequence of the fragmentary peptide consisting of the 172nd to 178th amino acids in SEQ ID NO: 2;

SEQ ID NO: 6 is the amino acid sequence of the fragmentary peptide consisting of the 238th to 244th amino acids in SEQ ID NO: 2;

SEQ ID NO: 7 is the amino acid sequence of the fragmentary peptide consisting of the 277th to 282nd amino acids in SEQ ID NO: 2;

SEQ ID NO: 8 is the amino acid sequence of the fragmentary peptide consisting of the 301st to 307th amino acids in SEQ ID NO: 2;

SEQ ID NO: 9 is the nucleotide sequence of the cDNA corresponding to the genomic RNA coding for the H protein of the virulent measles virus NA strain and the whole amino acid sequence encoded by the nucleotide sequence;

SEQ ID NO: 10 is the whole amino acid sequence of the H protein of the virulent measles virus NA strain;

SEQ ID NO: 11 is the amino acid sequence of the fragmentary peptide consisting of the 93rd to 616th amino acids in SEQ ID NO: 10;

SEQ ID NO: 12 is the amino acid sequence of the fragmentary peptide consisting of the 176th to 316th amino acids in SEQ ID NO: 10;

SEQ ID NO: 13 is the amino acid sequence of the fragmentary peptide consisting of the 172nd to 178th amino acids in SEQ ID NO: 10;

SEQ ID NO: 14 is the amino acid sequence of the fragmentary peptide consisting of the 238th to 244th amino acids in SEQ ID NO: 10;

SEQ ID NO: 15 is the amino acid sequence of the fragmentary peptide consisting of the 277th to 282nd amino acids in SEQ ID NO: 10;

SEQ ID NO: 16 is the amino acid sequence of the fragmentary peptide consisting of the 301st to 307th amino acids in SEQ ID NO: 10;

SEQ ID NO: 17 is the nucleotide sequence of the cDNA corresponding to the genomic RNA coding for the F protein of the attenuated measles virus CAM-70 strain and the whole amino acid sequence encoded by the nucleotide sequence;

SEQ ID NO: 18 is the whole amino acid sequence of the F protein of the attenuated measles virus CAM-70 strain;

SEQ ID NO: 19 is the nucleotide sequence of the cDNA corresponding to the genomic RNA coding for the F protein of the virulent measles virus NA strain and the whole amino acid sequence encoded by the nucleotide sequence; and SEQ ID NO: 20 is the whole amino acid sequence of the F protein of the virulent measles virus NA strain.

DETAILED DESCRIPTION OF THE INVENTION

In one aspect of the present invention, there is provided a measles virus mutant antigen, comprising at least one protein antigen selected from the group consisting of (I) a measles virus mutant H protein antigen and (II) a measles virus mutant F protein antigen, the measles virus mutant H protein antigen (I) being at least one member selected from the group consisting of the following amino acid sequences (a) to (f) identified with the positional amino acid numbers of either SEQ ID NO: 2 or SEQ ID NO: 10:

(a) the whole sequence of the 1st to 617th amino acids;

(b) a fragmentary sequence of the 93rd to 616th amino acids;

(c) a fragmentary sequence of the 176th to 316th amino acids;

(d) fragmentary sequences of the 172nd to 178th amino acids, the 238th to 244th amino acids, the 277th to 282nd amino acids, and the 301st to 307th amino acids;

(e) fragmentary, contiguous sequences of at least 6 amino acids in either SEQ ID NO: 2 or SEQ ID NO: 10, wherein the sequences each comprise an amino acid selected from the group consisting of the 174th, 176th, 243rd, 279th and 302nd amino acids, and neighboring amino acids of the selected amino acid in either SEQ ID NO: 2 or SEQ ID NO: 10, wherein the fragmentary, contiguous sequences are exclusive of the fragmentary sequences (d); and (f) fragmentary, contiguous sequences of at least 6 amino acids in either SEQ ID NO: 2 or SEQ ID NO: 10, wherein the sequences each comprise an amino acid selected from the group consisting of the 93rd, 157th, 169th, 175th, 211th, 252nd, 276th, 284th, 285th, 296th, 316th, 338th, 387th, 416th, 455th, 481st, 484th, 505th, 546th, 592nd, 600th, 603rd and 616th amino acids, and neighboring amino acids of the selected amino acid in either SEQ ID NO: 2 or SEQ ID NO: 10 wherein the fragmentary, contiguous sequences are exclusive of the fragmentary sequences (d) and (e); and the measles virus mutant F protein antigen (II) being at least one member selected from the group consisting of the following amino acid sequences (g) and (h) identified with the positional amino acid numbers of either SEQ ID NO: 18 or SEQ ID NO: 20:

(g) the whole sequence of the 1st to 550th amino acids; and (h) fragmentary, contiguous sequences of at least 6 amino acids in either SEQ ID NO: 18 or SEQ ID NO: 20, wherein the sequences each comprise an amino acid selected from the group consisting of the 11th, 52nd, 107th, 165th, 398th, 417th and 523rd amino acids, and neighboring amino acids of the selected amino acid in either SEQ ID NO: 18 or SEQ ID NO: 20.

For easy understanding of the present invention, the essential features and various preferred embodiments of the present invention are enumerated below.

1. A measles virus mutant antigen, comprising at least one protein antigen selected from the group consisting of (I) a measles virus mutant H protein antigen and (II) a measles virus mutant F protein antigen, the measles virus mutant H protein antigen (I) being at least one member selected from the group consisting of the following amino acid sequences (a) to (f) identified with the positional amino acid numbers of either SEQ ID NO: 2 or SEQ ID NO: 10:

(a) the whole sequence of the 1st to 617th amino acids;
(b) a fragmentary sequence of the 93rd to 616th amino acids;
(c) a fragmentary sequence of the 176th to 316th amino acids;
(d) fragmentary sequences of the 172nd to 178th amino acids, the 238th to 244th amino acids, the 277th to 282nd amino acids, and the 301st to 307th amino acids;
(e) fragmentary, contiguous sequences of at least 6 amino acids in either SEQ ID NO: 2 or SEQ ID NO: 10, wherein the sequences each comprise an amino acid selected from the group consisting of the 174th, 176th, 243rd, 279th and 302nd amino acids, and neighboring amino acids of the selected amino acid in either SEQ ID NO: 2 or SEQ ID NO: 10, wherein the fragmentary, contiguous sequences are exclusive of the fragmentary sequences (d); and
(f) fragmentary, contiguous sequences of at least 6 amino acids in either SEQ ID NO: 2 or SEQ ID NO: 10, wherein the sequences each comprise an amino acid selected from the group consisting of the 93rd, 157th, 169th, 175th, 211th, 252nd, 276th, 284th, 285th, 296th, 316th, 338th, 387th, 416th, 455th, 481st, 484th, 505th, 546th, 592nd, 600th, 603rd and 616th amino acids, and neighboring amino acids of the selected amino acid in either SEQ ID NO: 2 or SEQ ID NO: 10, wherein the fragmentary, contiguous sequences are exclusive of the fragmentary sequences (d) and (e); and the measles virus mutant F protein antigen (II) being at least one member selected from the group consisting of the following amino acid sequences (g) and (h) identified with the positional amino acid numbers of either SEQ ID NO: 18 or SEQ ID NO: 20:

(g) the whole sequence of the 1st to 550th amino acids; and (h) fragmentary, contiguous sequences of at least 6 amino acids in either SEQ ID NO: 18 or SEQ ID NO: 20, wherein the sequences each comprise an amino acid selected from the group consisting of the 11th, 52nd, 107th, 165th, 398th, 417th and 523rd amino acids, and neighboring amino acids of the selected amino acid in either SEQ ID NO: 18 or SEQ ID NO: 20.

2. A measles virus mutant gene, comprising at least one gene selected from the group consisting of (I) a gene coding for a measles virus mutant H protein antigen and (II) a gene coding for a measles virus mutant F protein antigen, the gene coding for a measles virus mutant H protein antigen (I) being at least one member selected from the group consisting of the following genes (a) to (f) identified with the positional amino acid numbers of either SEQ ID NO: 2 or SEQ ID NO: 10:

(a) a gene coding for the whole sequence of the 1st to 617th amino acids;
(b) a gene coding for a fragmentary sequence of the 93rd to 616th amino acids;
(c) a gene coding for a fragmentary sequence of the 176th to 316th amino acids;
(d) genes coding for fragmentary sequences of the 172nd to 178th amino acids, the 238th to 244th amino acids, the 277th to 282nd amino acids, and the 301st to 307th amino acids;
(e) genes coding for fragmentary, contiguous sequences of at least 6 amino acids in either SEQ ID NO: 2 or SEQ ID NO: 10, wherein the sequences each comprise an amino acid selected from the group consisting of the 174th, 176th, 243rd, 279th and 302nd amino acids, and neighboring amino acids of the selected amino acid in either SEQ ID NO: 2 or SEQ ID NO: 10, wherein the genes are exclusive of the genes (d); and
(f) genes coding for fragmentary, contiguous sequences of at least 6 amino acids in either SEQ ID NO: 2 or SEQ ID NO: 10, wherein the sequences each comprise an amino acid selected from the group consisting of the 93rd, 157th, 169th, 175th, 211th, 252nd, 276th, 284th, 285th, 296th, 316th, 338th, 387th, 416th, 455th, 481st, 484th, 505th, 546th, 592nd, 600th, 603rd and 616th amino acids, and neighboring amino acids of the selected amino acid in either SEQ ID NO: 2 or SEQ ID NO: 10, wherein the genes are exclusive of the genes (d) and (e); and the gene coding for measles virus mutant F protein antigen (II) being at least one member selected from the group consisting of the following genes (g) and (h) identified with the positional amino acid numbers of either SEQ ID NO: 18 or SEQ ID NO: 20:

(g) a gene coding for the whole sequence of the 1st to 550th amino acids; and (h) genes coding for fragmentary, contiguous sequences of at least 6 amino acids in either SEQ ID NO: 18 or SEQ ID NO: 20, wherein the sequences each comprise an amino acid selected from the group consisting of the 11th, 52nd, 107th, 165th, 398th, 417th and 523rd amino acids, and neighboring amino acids of the selected amino acid in either SEQ ID NO: 18 or SEQ ID NO: 20.

Hereinbelow, the present invention is described in detail.

In the present invention, with respect to the nucleotide sequences, A represents adenine, C represents cytosine, G represents guanine and T represents thymine.

In the present invention, with respect to the amino acid sequences, Ala represents an alanine residue, Arg represents an arginine residue, Asn represents an asparagine residue, Asp represents an aspartic acid residue, Cys represents a cysteine residue, Gln represents a glutamine residue, Glu represents a glutamic acid residue, Gly represents a glycine residue, His represents a histidine residue, Ile represents an isoleucine residue, Leu represents a leucine residue, Lys represents a lysine residue, Met represents a methionine residue, Phe represents a phenylalanine residue, Pro represents a proline residue, Ser represents a serine residue, Thr represents a threonine residue, Trp represents a tryptophan residue, Tyr represents a tyrosine residue and Val represents a valine residue.

For making more clear the essential features of the present invention, the technical features of the present invention will be described in detail below by explaining how the present invention has been developed.

All of the conventional live measles vaccines are produced from virus strains which were obtained by attenuating the viruses which prevailed in the 1950's and 1960's. Therefore, the antigenicity of conventional vaccine strains corresponds to the antigenicity of virus strains which were epidemic half a century ago.

On the other hand, it has been found that the most recent epidemic strains and the relatively recent epidemic strains have mutations in the H protein gene and the F protein gene which are genes responsible for a virion to adsorb on and penetrate into cells to thereby cause an infection with the virus. Specifically, the mutation in the H protein gene causes substitution of 17 to 19 amino acids in a specific region in the whole amino acid sequence (consisting of 617 amino acids) of the H protein and, such a substitution changes the three-dimensional structure of the protein, so that an antigenic mutation occurs. This antigenic mutation is as large as the antigenic shift of the H protein, and important.

Further, the present inventors have found that the antigenic mutation of the epidemic strain is an important factor causing the above-mentioned secondary vaccine failure and modified measles.

Based on these findings, the present inventors have succeeded in providing a viral genome of a measles virus mutant, particularly a mutant H protein gene and a mutant F protein gene, and the mutant antigens (not only the whole protein but also fragmentary peptides thereof) encoded by the genes.

In addition, the present inventors have successfully developed the following utilities (i) to (iii) of the above-mentioned genes, mutant antigens and their epitopes, and the like.

(i) Modification of a viral genome of a live vaccine strain: A recombinant virus is prepared by replacing the H protein gene of a conventional live vaccine strain with the H protein gene of an epidemic strain. By using this method, a live attenuated vaccine strain which is adapted for the antigenicity of the epidemic strain is obtained speedily. In other words, the recombinant virus obtained in the above-mentioned manner can be used as an active component of an excellent vaccine which is capable of effectively preventing infections with the epidemic strains. This a method is also advantageous from an economical view-point. That is, the time, labor and costs necessary for attenuating a virus can be decreased to a large extent. As mentioned above, with respect to the production of conventional vaccines, there is no specific limitation on the method for attenuating viruses, and conventionally, the attenuation was conducted mainly by passage, which requires at least several years to about 10 years for establishing an attenuated strain for a live vaccine.

(ii) Preparation of an active component for a gene vaccine: A gene vaccine is prepared by inserting the H protein gene and the F protein gene of an epidemic strain into various vectors, such as a plasmid vector, a cosmid vector, a phage vector, a shuttle vector, a viral vector of a non-proliferating viral vector and the like.

For example, when a non-proliferating recombinant virus, which is prepared by inserting the cDNAs for the above-mentioned H protein gene and F protein gene into a non-proliferating viral vector, is used as an active component for a gene vaccine or DNA vaccine, such a vaccine is capable of inducing both humoral immunity and cellular immunity like a conventional live measles vaccine. A remarkable feature of this vaccine is that nasal injection is possible.

In addition, a cDNA fragment comprising the mutated region of the H protein gene of an epidemic strain can be inserted into, for example, a plasmid vector, to prepare a naked DNA. The thus prepared naked DNA can also be used as an active component for a DNA vaccine or gene vaccine for preventing measles.

(iii) Preparation of a suitable reagent for diagnosis of epidemic strains: PCR primers are synthesize so that the synthesized primers reflect the mutations in the H protein gene or F protein gene of the epidemic strains. The synthesized primers can be used as a reagent for gene diagnosis not only for identifying the epidemic strains, but also for differentiating a virulent strain from an attenuated strain, or vice versa.

Further, the mutant antigens (whole proteins or fragmentary peptides thereof) encoded by the above-mentioned genes are prepared, and their epitopes are chemically synthesized. The antigens and epitopes are provided as suitable antigens for diagnosis of epidemic measles.

An explanation is made below with respect to the preparation of a measles virus mutant antigen and a measles virus mutant gene of the present invention, and the use of the prepared antigens and genes as a vaccine and a diagnostic reagent.

I Preparation of Measles Virus Mutant Antigen and Measles Virus Mutant Gene (1) Antigen analysis of various measles virus antigens: The antigenicity of the measles virus mutant antigen can be evaluated by a neutralization test, an HI (hemagglutination inhibition) test, a PA (passive agglutination) test, an enzyme immunoassay and a fluorescent antibody technique each using a monoclonal antibody, and the like. However, for determining the effectiveness of the virus antigen as antigen for a vaccine, it is requisite to evaluate the antibody titer by the neutralization test, and it can be performed in accordance with the modified Ueda method (Biken Journal, 14, 155–160, 1971) which employs microplates.

With respect to the antibodies used in the antigen analysis, sera, such as a serum from a measles patient and mouse immune sera against measles viruses as mentioned below, can be employed.

With respect to the antigens (challenge viruses) used in the antigen analysis, it is important to select different measles strains from the strains isolated in the past to the present. Representative examples of epidemic strains of the 1950's and 1960's (virulent strains of the past) include Tanabe strain and Edmonston strain; and examples of live vaccine strains established by attenuating the above-mentioned virulent strains (conventional attenuated strains) include CAM-70 strain and Edmonston B strain. As the recent epidemic strains (virulent strains), use can be made of the measles strains isolated in various countries in the 1990's. For example, the virus strains isolated from various resources by the present inventors, such as F-t strain (isolated in 1991 from throat swab of a reinfected patient), F-b strain (isolated in 1991 from blood of a reinfected patient), U-t strain (isolated in 1991 from throat swab of a non-vaccinated patient), U-b strain (isolated in 1991 from blood of a non-vaccinated patient), Momo strain (isolated in 1995 from a patient) and NA strain (isolated in 1996 from a patient) can be used as the recent epidemic strain.

Hereinafter, the following strains will be frequently referred to as indicated in the parentheses: Tanabe (Tana) strain, Edmonston (Edmo) strain, CAM-70 (CAM) strain and Momo (MO) strain.

(2) Determination of the mutated regions in the nucleotide sequence of a gene, and translation of the gene into an amino acid sequence: The analysis of the viral genome of each of the measles strains mentioned in item (1) above is carried out as follows. First, the viral RNA genome is extracted and the cDNA is prepared using primers. The nucleotide sequence of the prepared cDNA is determined by the direct sequencing method which employs PCR method (hereinafter, simply referred to as "PCR-direct sequencing method"). The search for DNA sequence homology between different measles virus strains is performed while determining the nucleotide sequence of the genes, to thereby specify the mutated regions within the genes.

Next, each of the above-specified mutated regions are translated into amino acid sequence in accordance with the universal code, and the deductive analyses of the amino acid sequences are performed as follows. Analysis of the hydrophobicity pattern and determination of the secondary structure of a protein by Chou-Fasman analysis are performed by computer using the computer software "DNASIS-Mac (version 3.6)" (manufactured and sold by Hitachi Software Engineering Co., Ltd., Japan). Epitopes can be identified, for example, by computer using the computer software "Epitope Advisor" [manufactured and sold by Fujitsu Kyushu System Engineering (FQS) Ltd., Japan].

(3) Measles virus mutant antigens and genes coding for the same: Based on the antigen analyses mentioned in item (1) above-and the studies on the nucleotide and amino acid sequences mentioned in item (2) above, the present inventors have conducted comparative analyses between the strains of recent epidemic measles, the virulent strains of the past and the conventional strains for a live attenuated measles vaccine, and they identified the respective regions in the H protein and the F protein which contain amino acid substitutions. Further, the present inventors specified the antigens useful for the vaccine or the reagent for diagnosis of epidemic strain of measles virus. The measles virus mutant antigen of the present invention is the whole protein or a fragmentary peptide of the H protein and F protein of the attenuated measles virus CAM-70 strain or the epidemic measles virus NA strain. Each of the amino acid sequences is disclosed for the first time by the inventors of the present invention. Specifically, the measles virus mutant antigen of the present invention is an antigen comprising at least one protein antigen selected from the group consisting of (I) an H protein antigen of a measles mutant and (II) an F protein antigen of a measles mutant.

The measles virus mutant H protein antigen (I) is at least one member selected from the group consisting of the following amino acid-sequences (a) to (f) identified with the positional amino acid numbers of either SEQ ID NO: 2 or SEQ ID NO: 10:

(a) the whole sequence of the 1st to 617th amino acids;

(b) a fragmentary sequence of the 93rd to 616th amino acids;

(c) a fragmentary sequence of the 176th to 316th amino acids;

(d) fragmentary sequences of the 172nd to 178th amino acids, the 238th to 244th amino acids, the 277th to 282nd amino acids, and the 301st to 307th amino acids;

(e) fragmentary, contiguous sequences of at least 6 amino acids in either SEQ ID NO: 2 or SEQ ID NO: 10, wherein the sequences each comprise an amino acid selected from the group consisting of the 174th, 176th, 243rd, 279th and 302nd amino acids, and neighboring amino acids of the selected amino acid in either SEQ ID NO: 2 or SEQ ID NO: 10, wherein the fragmentary, contiguous sequences are exclusive of the fragmentary sequences (d); and (f) fragmentary, contiguous sequences of at least 6 amino acids in either SEQ ID NO: 2 or SEQ ID NO: 10, wherein the sequences each comprise an amino acid selected from the group consisting of the 93rd, 157th, 169th, 175th, 211th, 252nd, 276th, 284th, 285th, 296th, 316th, 338th, 387th, 416th, 455th, 481st, 484th, 505th, 546th, 592nd, 600th, 603rd and 616th amino acids, and neighboring amino acids of the selected amino acid in either SEQ ID NO: 2 or SEQ ID NO: 10, wherein the fragmentary, contiguous sequences are exclusive of the fragmentary sequences (d) and (e).

The measles virus mutant F protein antigen (II) is at least one member selected from the group consisting of the following amino acid sequences (g) and (h) identified with the positional amino acid numbers of either SEQ ID NO: 18 or SEQ ID NO: 20:

(g) the whole sequence of the 1st to 550th amino acids; and (h) fragmentary, contiguous sequences of at least 6 amino acids in either SEQ ID NO: 18 or SEQ ID NO: 20, wherein the sequences each comprise an amino acid selected from the group consisting of the 11th, 52nd, 107th, 165th, 398th, 417th and 523rd amino acids, and neighboring amino acids of the selected amino acid in either SEQ ID NO: 18 or SEQ ID NO: 20.

Among the protein antigens included in the measles virus mutant antigens of the present invention, the protein antigens as defined in items (a) and (g) above are H protein and F protein, respectively, and the protein antigens as defined in items (b) to (f) and (h) above are peptides (fragmentary sequences). Further, the four fragmentary sequences as defined in item (d) above, namely, the fragmentary sequences of the 172nd to 178th amino acids, the 238th to 244th amino acids, the 277th to 282nd amino acids, and the 301st to 307th amino acids, identified with the positional amino acid numbers of either SEQ ID NO: 2 or SEQ ID NO: 10, are epitopes of the H protein which are disclosed for the first time by the inventors of the present invention. With respect to the protein antigens as defined in items (a) to (d) and (g) above, the specific sequences are shown in the Sequence Listing. Each of the antigens of the present invention can be chemically synthesized, based on the sequences shown in the Sequence Listing (see Example 5).

The measles virus mutant antigen of the present invention comprises at least one protein antigen selected from the group consisting of the above-mentioned whole proteins and fragmentary peptides, and the protein antigen can be chosen, based on the intended utility of the measles virus mutant antigen. Occasionally, several protein antigens can be used in combination.

In a further aspect of-the present invention, a gene coding for the above-mentioned measles virus mutant antigen is provided. Specifically, the measles virus mutant gene comprising at least one gene selected from the group consisting of (I) a gene coding for an H protein antigen of a measles mutant and (II) a gene coding for an F protein antigen of a measles mutant is provided.

The gene (I) coding for a measles virus mutant H protein antigen is at least one member selected from the group consisting of the following genes (a) to (f) identified with the positional amino acid numbers of either SEQ ID NO: 2 or SEQ ID NO: 10:

(a) a gene coding for the whole sequence of the 1st to 617th amino acids;

(b) a gene coding for a fragmentary sequence of the 93rd to 616th amino acids;

(c) a gene coding for a fragmentary sequence of the 176th to 316th amino acids;

(d) genes coding for fragmentary sequences of the 172nd to 178th amino acids, the 238th to 244th amino acids, the 277th to 282nd amino acids, and the 301st to 307th amino acids;

(e) genes coding for fragmentary, contiguous sequences of at least 6 amino acids in either SEQ ID NO: 2 or SEQ ID NO: 10, wherein said sequences each comprise an amino acid selected from the group consisting of the 174th, 176th, 243rd, 279th and 302nd amino acids, and neighboring amino acids of the selected amino acid in either SEQ ID NO: 2 or SEQ ID NO: 10, wherein the genes are exclusive of the genes (d); and (f) genes coding for fragmentary, contiguous sequences of at least 6 amino acids in either SEQ ID NO: 2 or SEQ ID NO: 10, wherein said sequences each comprise an amino acid selected from the group consisting of the 93rd, 157th, 169th, 175th, 211th, 252nd, 276th, 284th, 285th, 296th, 316th, 338th, 387th, 416th, 455th, 481st, 484th, 505th, 546th, 592nd, 600th, 603rd and 616th amino acids, and neighboring amino acids of the selected amino acid in either SEQ ID NO: 2 or SEQ ID NO: 10, wherein the genes are exclusive of the genes (d) and (e).

The gene (II) coding for measles virus mutant F protein antigen is at least one member selected from the group consisting of the following genes (g) and (h) identified with the positional amino acid numbers of either SEQ ID NO: 18 or SEQ ID NO: 20:

(g) a gene coding for the whole sequence of the 1st to 550th amino acids; and (h) genes coding for fragmentary, contiguous sequences of at least 6 amino acids in either SEQ ID NO: 18 or SEQ ID NO: 20, wherein the sequences each comprise an amino acid selected from the group consisting of the 11th, 52nd, 107th, 165th, 398th, 417th and 523rd amino acids, and neighboring amino acids of the selected amino acid in either SEQ ID NO: 18 or SEQ ID NO: 20.

With respect to the gene coding for the measles virus mutant antigen of the present invention, there is no particular limitation as long as the gene codes for the whole protein or a fragmentary peptide of the measles virus mutant antigen. Therefore, the gene is not limited to the nucleotide sequence of the genomic RNA of CAM-70 strain or NA strain. As the measles virus mutant gene, use can be made of the cDNAs shown in SEQ ID NOs: 1, 9, 17 and 19, or the gene can be prepared by synthesizing a nucleotide sequence on the basis of an amino acid sequence of a measles virus mutant antigen.

The measles virus mutant gene of the present invention comprises at least one gene selected from the group consisting of the above-mentioned genes, and the gene can be chosen, based on the intended utility of the measles virus mutant gene. Like the measles virus mutant antigen of the present invention, the measles virus mutant gene of the present invention comprises both the genes of the attenuated strain and the genes of the epidemic strain. Based on the disclosure of the present invention, for example, a live vaccine effective for preventing the infection with the epidemic strains can be produced {see the below-mentioned item [II](1), and Examples 2 and 3}. When several genes are used in combination, they can also be used in such a form as ligated to each other {see the below-mentioned item [II](2) and Example 4}.

The antigens and genes coding for the same of the present invention, which respectively comprise the above-mentioned sequences, are effective as a marker for identifying a virulent strain or an attenuated strain, and are also important and advantageous for improving conventional vaccines and developing diagnostic reagents.

II Use of Measles Virus Mutant Antigen and Measles Virus Mutant Gene of the Present Invention as Vaccine and Diagnostic Reagent (1) Preparation of an effective live vaccine for epidemic measles strains: A recombinant virus is prepared by replacing a gene of a live vaccine strain with a corresponding gene of an epidemic strain. With respect to the live vaccine strain, various strains mentioned under "Prior Art" of the specification can be used, but preferably, use is made of a strain which has been employed as an active component of a live vaccine in various countries for at least 10 years. That is, a strain having approved safety and effectiveness as an active component for a vaccine, such as CAM-70 strain, is preferred.

With respect to the epidemic strain used for preparing a live vaccine, the epidemic strain is selected so that when the selected strain is compared with a live vaccine strain, the epidemic strain has a marked, broad antigenic mutation due to the genetic mutation thereof. Specifically, a preferred epidemic strain is a recent epidemic strain which is being isolated at high frequency and is widely prevailing, and which has a universal antigenic mutation (that is, an antigenic mutation which is not peculiar to a particular strain), for example, MO strain or NA strain isolated by the inventors of the present invention in 1995 to 1996.

With respect to the gene to be used for replacement, the gene can be selected from the genes coding for the antigens mentioned in item [I](3) above, and the genes can be used individually or in combination. However, for preventing any possible reversion of a recombinant virus from an attenuated state to a virulent state, and also from the viewpoint of ease in preparing a recombinant virus, it is preferred to use the gene described in item (c), that is, the gene coding for the fragmentary sequence of the 176th to 316th amino acids of the H protein (the peptide of SEQ ID NO: 4 and the peptide of SEQ ID NO: 12). The amino acid substitutions in this region are characteristic of the epidemic strains and such substitutions are not found in the H protein of the attenuated strains. Therefore, by using the gene coding for this region, an epitope of the epidemic strain can be introduced into the attenuated strain without changing the sequences which are characteristic of the attenuated strains (that is, the sequences which may be causative of attenuation).

The recombinant virus can be produced by the method of Radecke et al. (EMBO Journal, Vol. 14, No. 23, pp. 5773–5784, 1995) which is a method for genetic recombination of a non-segmented negative-strand RNA viral (mononegaviral) genome, or by the modified method of Radecke et al., which has been developed by the inventors of the present invention.

The method of Radecke et al. (frequently referred to as "reverse genetics") will be explained below. First, the cells of 293 cell line (American Type Culture Collection, Accession No. ATCC CRL-1573) were transfected with a recombinant vector containing genes coding for T7 RNA polymerase and measles virus N protein and P protein, thereby obtaining transfectants (i.e., helper cells) capable of expressing T7 RNA polymerase, N protein and P protein. Next, an expression vector capable of expressing L protein (polymerase) of the measles virus under the control of T7 promoter is constructed (hereinafter, the constructed expression vector is simply referred to as "V1"). Further, a cDNA for the (+) sense RNA of the whole genome of CAM-70 strain is prepared, and a DNA fragment coding for a region in the H protein which contains the above-mentioned amino acid substitutions is cleaved and removed from the cDNA for CAM-70 strain by means of restriction enzymes. Then, the DNA sequence of the corresponding region of the viral genome of epidemic MO strain or NA strain is prepared therefrom and inserted into the restriction site of the cDNA for CAM-70 strain, to thereby obtain a recombinant cDNA. The obtained recombinant cDNA is inserted into plasmid pBluescript SK or KS (manufactured and sold by Stratagene Co., Ltd., England), thereby obtaining an expression vector (hereinafter, the obtained expression vector is simply referred to as "V0"), wherein the expression vector is prepared so that the recombinant cDNA is capable of transcription by T7 RNA polymerase. V0 and V1 are co-transfected to the helper cells prepared above, and the desired recombinant measles virus can be obtained by subsequently culturing the transfected cells. The proliferation of the recombinant virus in the transfected cells can be confirmed by detecting the occurrence of CPE (cytopathic effect), wherein the transfected cells generate syncytia, or by conducting a microscopic observation using a fluorescent antibody technique with a monoclonal antibody against the epitope of the protein encoded by the replaced gene.

The recombinant attenuated measles virus of CAM-70 strain, in which the gene coding for the 176th to 316th amino acids of the H protein of CAM-70 strain (SEQ ID NO: 4) is replaced by the gene coding for the 176th to 316th amino acids of the H protein of MO strain or NA strain (SEQ ID NO: 12), is obtained by using the above-mentioned method.

Further, the modified method of Radecke et al. is explained below. This modified method is such that the helper cells are not required, and any desired permissive cells can be used as host cells for the recombinant virus. With respect to the host cells employed, cells which are ensured to be safe as a culture host for the live vaccine strains and are approved as the host cells therefor, such as, MRC-5 cells and WI-38 cells are preferably used to prevent an introduction of an unidentified factor, a carcinogen and the like into the virus. First, the expression vectors for each of the genes coding for N, P, and L proteins of CAM-70 strain are individually prepared using plasmids pcDNA3.1 (+) or pcDNA3.1(−) (manufactured and sold by Invitrogen Co., Ltd., Canada). For example, each of the genes encoding N, P and L proteins of CAM-70 strain is individually inserted into an appropriate restriction site of pcDNA3.1(−), thereby constructing the expression vectors. For the expression of T7 RNA polymerase, recombinant MVA (hereinafter, simply referred to as "recMVA"; FEBS Letter, vol. 371, no. 1, pp. 9–12, 1995) can be used. The above-prepared three expression vectors and the expression vector V0 mentioned in connection with the method of Radecke et al. are co-transfected to either the MRC-5 cells or WI-38 cells which have already been transfected with recMVA. The desired recombinant attenuated measles virus is obtained by culturing the transfected cells at about 35° to 38° C. The proliferation of the virus can be confirmed by detecting the occurrence of CPE or by conducting the microscopic observation using the fluorescent monoclonal antibody technique mentioned above. Further, the antigenicity and immunogenicity of the obtained recombinant virus can be qualified in accordance with the antigen analysis mentioned in item [I](1) above.

(2) Preparation of an active component of a gene vaccine: The non-proliferating recombinant adenovirus can be prepared by inserting a gene of an epidemic measles virus into a non-proliferating adenoviral genome. The prepared recombinant adenovirus is effective as an active component of a gene vaccine. For preparing the recombinant virus, COS-TPC method developed by Saito et al. [Cell Technology (Saibo Kogaku), vol. 13, no. 8, pp. 757–763, 1994] can be employed. In this method, DNA-TPC (viral DNA-Terminal Protein Complex) of the genome of human adenovirus 5, and a cassette cosmid carrying almost all of the whole genome of the non-proliferating adenovirus (cassette cosmid pAdexl; U.S. Pat. No. 5,700,470) are used. The non-proliferating adenovirus is derived from human adenovirus 5 and it lacks E1A and E1B genes which are essential for viral proliferation, and therefore, this virus is incapable of proliferation in cells other than the 293 cells which constantly express E1A and E1B genes. Further, this virus lacks gene coding for E3 protein, a protein which antagonizes the recognition of viral antigens by CTL (cytotoxic T lymphocytes). Due to this contrived design of the adenovirus, cellular immunity induced by CTL is expected to develop even in the presence of this virus.

With respect to a measles virus gene used for preparing the recombinant virus, the gene can be selected from the genes coding for the antigens mentioned in item [I](3) above, and the genes can be used individually or in combination. However, for improving the immunogenicity which is necessary for providing a protection against the viral infection (that is, adsorption and penetration of a measles virus to a cell), it is preferred to use in combination the gene coding for the whole H protein mentioned in item (a) (SEQ ID NO: 2 or SEQ ID NO: 10) and the gene coding for the whole F protein mentioned in item (g) (SEQ ID NO: 18 or SEQ ID NO: 20).

Specifically, the cDNAs for the above mentioned H protein gene and F protein gene (for example, the nucleotide sequences of SEQ ID NO: 9 and SEQ ID NO: 19) are prepared [when the cDNAs are ligated, they are ligated in the order of H protein—F protein (HF) or F protein—H protein (FH) in the direction of from the 5' end to the 31 end], and the prepared cDNAs are inserted into the E1A·E1B deletion site of the cassette cosmid pAdex1, to thereby obtain recombinant cosmid pAdex1/HF or pAdex1/FH. On the other hand, DNA-TPC is extracted from the parent adenovirus strain, and the DNA-TPC is digested with the restriction enzyme Eco T22I (manufactured and sold by Takara Shuzo Co., Ltd., Japan), to thereby obtain digestion product DNA-TPC/Eco T22I. Subsequently, pAdex1/HF or pAdex1/FH, and DNA-TPC/Eco T22I are co-transfected to the 293 cells by calcium phosphate method. As a result of the co-transfection, homologous recombination between the transfected DNAs occurs in the cells, and a non-proliferating recombinant adenovirus containing measles virus H protein gene and F protein gene is obtained. The presence of measles virus H and F proteins in the non-proliferating recombinant adenovirus can be confirmed by testing Hela cells infected with the obtained adeno-virus by fluorescent antibody technique using the monoclonal antibodies against the measles proteins.

(3) Production of a measles vaccine: The live attenuated measles vaccine can be produced by using the recombinant attenuated measles virus mentioned in item [II](1) above as a seed virus. For example, the recombinant virus is proliferated in permissive cells, such as chicken embryo cells, thereby obtaining a virus suspension. The cells are removed from the obtained virus suspension by low-speed centrifugation, thereby obtaining a supernatant. Then, the obtained supernatant is subjected to filtration to thereby prepare a bulk vaccine solution. The prepared bulk vaccine solution is diluted with a medium, such as BME medium (Eagle's Basal Medium), so as to obtain a vaccine solution comprising the virus in a sufficient antigenic amount, for example, not less than 5,000 $TCID_{50}$ (Median Tissue Culture Infective Dose) per 0.5 ml of vaccine solution. A stabilizer for stabilizing the virus can be added to the vaccine solution when the bulk vaccine solution is being diluted. Subsequently, the diluted vaccine solution is dispensed into suitable containers, such as 1 to 20 ml volume vials, and then, the containers are sealed hermetically, and the sealed vaccine is provided as a vaccine preparation. The vaccine preparation can be provided as a liquid preparation or as a lyophilized preparation obtained by lyophilizing the vaccine after dispensation. Prior to the use of the vaccine preparation, it is requisite to subject the vaccine preparation to various tests on effectiveness and safety to assure its quality as a vaccine. The tests are conducted in accordance with Pharmaceutical Affairs Law (the Law No. 145 established in 1960) and a provision entitled "Dried Attenuated Measles Virus Live Vaccine" in the Notification No. 217 of the Japanese Ministry of Health and Welfare: Seibutsugakuteki Seizai Kijun (Minimum Requirements for Biological Products) established in 1993. With respect to the manner of administration, for example, the vaccine preparation is administrated by subcutaneous injection in an amount of 0.25 to 0.5 ml per dose.

The non-proliferating recombinant virus mentioned in item [II](2) above can be produced in large yield using the 293 cells. The recombinant virus can be prepared from the liquid culture of 293 cells in substantially the same manner as mentioned above for preparing the vaccine preparation, so that the final virus content of a liquid or lyophilized preparation is $10^6$ to $10^8$ PFU (plaque-forming unit) per 1 ml of preparation. Such virus preparation can be provided as an active component for a gene vaccine. With respect to the manner of administration, the gene vaccine can be administered by subcutaneous, intramascular or nasal injection in an amount of 0.25 to 0.5 ml per dose, and from the viewpoint of ease in injection procedure, nasal injection is especially preferred.

(4) Preparation of a diagnostic reagent: The antigens mentioned in item [I](3) above (whole protein or fragmentary peptide thereof) can be used individually or in combination as an antigen for diagnosis. When using several antigens in combination, the antigens containing different epitopes are preferably used to broaden the spectrum of reactivity with antibody. The antigen of the present invention can be provided as an antigen to be used in various diagnoses, such as diagnosis using precipitation reaction, agglutination reaction, neutralization reaction, fluorescent antibody technique, enzyme immunoassay, and radioimmunoassay. Further, the antigens can be inoculated intraperitoneally, subcutaneously or intramuscularly to an animal, such as rabbit, guinea pig and mouse, to prepare an immune serum, antibody or the like. The thus prepared antibody can be also provided as an antibody for detecting antigens in various diagnoses.

The antigen or antibody of the present invention is diluted so as to prepare a diagnostic reagent containing the antigen or antibody in an amount sufficient to cause an antigen-antibody reaction.

Further, the genes coding for the antigen mentioned in item [I](3) above can be used individually or in combination, for example, as a probe reagent for gene diagnosis and a reagent for identifying the measles virus strains. PCR primers can be designed, based on the amino acid sequences of the H protein and F protein of the attenuated strain and epidemic strain (for example, SEQ ID NOs: 2, 10, 18 and 20) and based the nucleotide sequences of the genes coding for the same (for example, SEQ ID NOs: 1, 9, 17 and 19) which are disclosed in the present specification. Such PCR primers can be provided as a reagent for diagnosis using the PCR method.

BEST MODE FOR CARRYING OUT THE INVENTION

Hereinbelow, the present invention will be described in more detail with reference to the following Examples, but they should not be construed as limiting the scope of the present invention.

EXAMPLE 1

Antigen analyses and gene analyses are performed as follows, to thereby identify the differences in nucleotide sequences and amino acid sequences between the past epidemic strains (virulent strains), conventional live vaccine strains (attenuated strains) and recent epidemic strains (virulent strains). In addition, the amino acid sequences of mutant antigens and their epitopes are determined.

(1) Antigen Analyses

Measurement of Neutralizing Antibody Titers (1):

Each of the neutralizing antibody titers for a vaccine strain and an epidemic strain in a test serum is measured separately by the modified Ueda method which employs microplates. As a challenge virus, CAM-70 strain is used as a vaccine strain, and Momo strain is used as an epidemic strain. B95a cells are used for proliferating the viruses. The test sera are selected from sample sera individually obtained from infants who received vaccination with measles CAM-70 strain vaccine during the period of 1994 to 1996, in which the sera were sampled from each infant before the vaccination and 1 to 2 months after the vaccination. Two groups of test sera (i.e., groups A and B) are prepared, so that group A consists of eleven (11) sample sera each having HI (hemagglutination inhibition) antibody titer of 8-fold, and group B consists of fourteen (14) sample sera each having HI antibody titer of 64-fold, both measured using HI antigen of Toyoshima strain (isolated in 1959). Two rows of microplate wells were used for determining the neutralizing antibody titer in a test serum.

20 μl of culture medium is dispensed into each well of a microplate, and serial 2-fold dilution of each test serum (20 μl) with the dispensed culture medium is performed. 20 μl of a challenge virus solution (viral infective dose is already adjusted to 10 $TCID_{50}$/20 μl) is placed in each well and mixed with the diluted test serum, and then, a reaction is allowed to proceed at 37° C. for 1 hour. Subsequently, 100 μl of cultured B95a cells is added to each reaction mixture in the well, and the cells are cultured for 1 week. The neutralizing antibody titer is measured by detecting the occurrence of CPE (cytopathic effect). The results are shown below.

Group A: The relative antibody titer (antibody titer for epidemic strain/antibody titer for vaccine strain) is less than ½ in nine (9) test sera out of the total of eleven (11) test sera (9/11; 81.8%). Particularly, among the above-mentioned nine (9) test sera, the antibody titer for the epidemic strain is not detected (that is, the value of antibody titer is less than 0 as expressed in terms of $log_2$) in six (6) test sera (6/11; 54.5%), even though the antibody titer for the vaccine strain is from 2.6 to 3.6 (the values are expressed in terms of $log_2$) in these test sera. With respect to the remaining two (2) test sera, the relative antibody titer is 1 (i.e., 1/1).

Group B: With respect to ten (10) test sera out of the total of fourteen (14) test sera (10/14; 71.4%), the relative antibody titer (antibody titer of epidemic strain/antibody titer of vaccine strain) is so low as to fall within the range of from ½ to ⅛. Each of the remaining four (4) test sera has a relative antibody titer of approximately 1 (i.e., 1/1). Since test sera having a relative antibody titer (antibody titer of epidemic strain/antibody titer of vaccine strain) of less than ½ are frequently found among the sera containing antibodies against a conventional measles virus, it is concluded that the recent epidemic strain has certain mutation in its antigens (that is, both the H and F proteins) which are related to the neutralization of antibodies and viral infection.

Measurement of Neutralizing Antibody Titers (2):

The neutralizing antibody titers in a mouse immune serum against the H protein of NA strain is determined in substantially the same manner as mentioned in measurement (1) above, except that CAM-70 strain, Tanabe strain and NA strain are separately used as a challenging virus, and the mouse immune sera prepared in the following manner are used as the test sera.

Ten BALB/C mice (4 weeks old) are individually injected intramuscularly with 100 μl of a solution of expression vector pcDNA3.1(−)/H capable of expressing the H protein of NA strain (hereinafter, simply referred to as "naked DNA"). After 2 weeks from the first injection, as a booster injection, the intramuscular injection of the naked DNA is repeated in substantially the same manner as the first injection. As a control, physiological saline is injected instead of the naked DNA to each of the five mice in substantially the same manner as mentioned above. After 4 weeks from the booster injection, blood is sampled individually from each of the ten immunized mice and five control mice to thereby obtain mouse immune sera.

The above-mentioned naked DNA is the expression vector for NA strain H protein prepared in connection with Example 3 below, and it is obtained by amplifying plasmid pcDNA3.1(−)/H in *E. coli*, and substantially purifying the plasmid from the *E. coli* culture.

As a result, it is found that the average neutralizing antibody titer (the value expressed in terms of $\log_2$) for NA strain, CAM-70 strain and Tanabe strain is 4.0, 3.8 and 4.0, respectively. From the above results and the results of measurement (1) mentioned above, it is concluded that the antigen of the recent epidemic strain (i.e., NA strain) has a broader spectrum with respect to the reactivity with antibody than that of the vaccine strain or the epidemic strain of the past, and that the antigenicities of the vaccine strain and the past epidemic strain are embraced by that of the recent epidemic strain.

(2) Gene Analyses

Determination of the nucleotide sequences of the H protein and F protein:

The nucleotide sequences of the H and F proteins are determined in accordance with the method of Isegawa et al. (Mol. Cell. Prob., 6, 467–475, 1992). Each of the measles strains shown in Tables 2 and 3 is infected individually to B95a cells, and RNA is extracted from each of the infected cells by GTC/CsCl method of Chirgwin et al. (Biochemistry, 18, 5294–5299, 1979). Subsequently, the cDNA for each measles strain is synthesized using random primers (6 mer). Based on the cDNA sequence of the gene of Edmonston strain (Virology, vol. 173, no. 2, pp. 415–425, 1989), specific primers (shown in Table 1) are synthesized, and the nucleotide sequence of each of the measles strains is determined by the PCR-direct sequencing method using the synthesized primers. The amino acid sequence is deduced from each nucleotide sequence in accordance with the universal code, and in addition, the amino acids which are substituted as a result of genetic mutations are identified. The results are shown in Tables 2 and 3 and SEQ ID NOs: 1, 2, 9, 10, and 17 to 20.

TABLE 1

Primers used for PCR-direct sequencing method

| | Primer | Nucleic acid sequence |
|---|---|---|
| Gene coding for F protein | F28(SEQ ID NO:21) | AGAATCAAGACTCATCCAATGTC |
| | CF7(SEQ ID NO:22) | TTGAGAGTTCAGCATGGACTGGT |
| | CF3(SEQ ID NO:23) | ACAATGAAGTAGGACTCTGTGTC |
| | F3(SEQ ID NO:24) | GGAACCTAATAGCCAATTGTGCA |
| | CF2(SEQ ID NO:25) | CGAGGTCAATTCTGTGCAAGTAC |
| | F4(SEQ ID NO:26) | AAAGGGAGAACAAGTTGGTATGT |
| | CF1(SEQ ID NO:27) | GATATTGTTCGGCCAGAGGGAAG |

TABLE 1-continued

Primers used for PCR-direct sequencing method

|  | Primer | Nucleic acid sequence |
|---|---|---|
| Gene coding for<br>H protein | MP5(SEQ ID NO:28)<br>MP4(SEQ ID NO:29)<br>MP2(SEQ ID NO:30)<br>H8(SEQ ID NO:31)<br>MP3(SEQ ID NO:32) | ATGTCACCACAACGAGACCGGAT<br>GAGATTCACTGACCTAGTGAAAT<br>TCGCTGTCCCTGTTAGACTTGTA<br>GAGCAACCAGTCAGTAATGATCT<br>ATGCCTGATGTCTGGGTGACATC |

TABLE 2

Amino acid substitutions in H protein

| Amino acid number | Measles strain | | | | | | | | |
|---|---|---|---|---|---|---|---|---|---|
|  | Edmo | Tana | CAM-70 | F-b | F-t | U-b | U-t | MO | NA |
| 93 | Thr |  | Ile |  |  |  |  |  |  |
| 157 | Val |  | Ala |  |  |  |  |  |  |
| 169 | Ser |  |  | Ala | Ala | Ala | Ala | Ala | Ala |
| 174 | Thr |  |  | Ala | Ala | Ala | Ala | Ala | Ala |
| 175 | Arg | Lys | Lys |  |  |  |  |  |  |
| 176 | Thr |  |  | Ala | Ala | Ala | Ala | Ala | Ala |
| 211 | Gly |  |  | Ser | Ser | Ser | Ser | Ser | Ser |
| 243 | Arg |  |  | Gly | Gly | Gly | Gly | Gly | Gly |
| 252 | Tyr |  |  | His | His | His | His | His | His |
| 276 | Leu |  |  | Phe | Phe | Phe | Phe | Phe | Phe |
| 279 | Pro |  |  | Ser | Ser | Ser | Ser | Ser | Ser |
| 284 | Leu |  |  | Phe | Phe | Phe | Phe | Phe | Phe |
| 285 | Ser |  |  |  |  |  |  | Asn | Asn |
| 296 | Leu |  |  | Phe | Phe | Phe | Phe | Phe | Phe |
| 302 | Gly |  |  | Arg | Arg | Arg | Arg | Arg | Arg |
| 316 | Gly |  |  | Ser | Ser | Ser | Ser |  |  |
| 338 | Pro |  | Ser |  |  |  |  |  |  |
| 387 | Leu |  |  |  |  |  |  |  | Gln |
| 416 | Asp |  |  | Asn | Asn | Asn | Asn | Asn | Asn |
| 455 | Thr |  | Asn |  |  |  |  |  |  |
| 481 | Tyr |  |  | Asn | Asn | Asn | Asn | Asn | Asn |
| 484 | Asn | Thr | Thr | Thr | Thr | Thr | Thr | Thr | Thr |
| 505 | Asp |  | Gly |  |  |  |  |  |  |
| 546 | Ser | Gly |  |  |  |  |  |  |  |
| 592 | Gly | Glu | Glu |  |  |  |  |  |  |
| 600 | Glu | Val | Val | Val | Val | Val | Val | Val | Val |
| 603 | Gly |  | Glu |  |  |  |  |  |  |
| 616 | Arg |  |  | Ser | Ser | Ser | Ser | Ser | Ser |

[Note]
(1) "Edmo" represents "Edmonston strain", "Tana" represents "Tanabe strain", and "MO" represents "Momo strain".
(2) Amino acid sequence of H protein (deduced from cDNA) of Edmonston strain is used as a standard for determining the substituted amino acids in H protein of other measles strains. Amino acids which are the same as that of the Edmonston strain are not shown.

TABLE 3

Amino acid substitutions in F protein

| Amino acid number | Measles strain | | | | | | | | |
|---|---|---|---|---|---|---|---|---|---|
|  | Edmo | Tana | CAM-70 | F-b | F-t | U-b | U-t | MO | NA |
| 11 | Phe |  | Ile |  |  |  |  | Leu | Leu |
| 52 | Gln | His | His |  |  |  |  |  |  |
| 107 | Ser | Gly | Gly |  |  |  |  |  |  |
| 165 | Arg |  | Gly |  |  |  |  |  |  |
| 398 | tyr |  | His |  |  |  |  |  |  |

TABLE 3-continued

Amino acid substitutions in F protein

| Amino acid number | Measles strain | | | | | | | |
|---|---|---|---|---|---|---|---|---|
| | Edmo | Tana | CAM-70 | F-b | F-t | U-b | U-t | MO | NA |
| 417 | Ala | Asp | Asp | | | | | | |
| 523 | Lys | | | Arg | Arg | Arg | Arg | Arg | Arg |

[Note]
(1) "Edmo" represents "Edmonston strain", "Tana" represents "Tanabe strain", and "MO" represents "Momo strain".
(2) Amino acid sequence of F protein (deduced from cDNA) of Edmonston strain is used as a standard for determining the substituted amino acids in F protein of other measles strains. Amino acids which are the same as that of the Edmonston strain are not shown.

Determination of the Secondary Structure of the H Protein:

The secondary structure of the H protein is determined by analyzing the above-identified amino acid sequence by computer. Computer software "DNASIS-Mac (version 3.6)" (manufactured and sold by Hitachi Software Engineering Co., Ltd., Japan) is used to analyze the hydrophobicity pattern and to conduct Chou-Fasman analysis. As a result, with respect to the secondary structure of each of the regions respectively consisting of the 176th to 316th amino acids and the 317th to 616th amino acids of the whole amino acid sequence of the H protein shown in SEQ ID NO: 2, the positions of epitopes are flip-flopped between the vaccine strain and the epidemic strain [that is, when an analytical diagram for a vaccine strain (for example, CAM-70 strain) and an analytical diagram for an epidemic strain (for example, MO strain or NA strain) are arranged side by side, it is apparent that the diagram for the epidemic strain is transformed to look like a mirror image (axial symmetry) of the diagram for the vaccine strain]. On the other hand, with respect to the F protein, when the analytical diagrams are prepared for a vaccine strain and an epidemic strain, no such differences as would cause a mirror image (axial symmetry) are observed.

Analysis of the Mutated Epitopes of the H Protein:

With respect to the amino acid sequences of the above-mentioned vaccine strain and epidemic strain, the regions where the mutation (amino acid substitutions) is concentrated are analyzed by computer using the computer software "Epitope Advisor" [manufactured and sold by Fujitsu Kyushu System Engineering (FQS) Co., Ltd., Japan] to determine the epitopes. As a result, the following four regions, the 172nd to 178th amino acids, the 238th to 244th amino acids, the 277th to 282nd amino acids, and the 301st to 307th amino acids, identified with the positional amino acid numbers of either SEQ ID NO: 2 or SEQ ID NO: 10, are determined as the mutated epitope regions of the H protein.

EXAMPLE 2

Modification of a Genome of a Live Attenuated Vaccine Strain:

A recombinant CAM-70 virus, which is vaccine virus CAM-70 strain having a part of its H protein replaced by the corresponding part of the H protein of epidemic measles Momo strain, is prepared by the method of Radecke et al. (reverse genetics) described in item [II](1) above.

The part of the H protein to be replaced is the restriction enzyme HinfI fragment of the cDNA derived from the viral genome comprising the region consisting of the 526th to 948th nucleotides (total of 423 nucleotides) of the nucleotide sequence of SEQ ID NO: 1 (encoding the 176th to 316th amino acids of H protein). The antigenicity of the prepared recombinant virus is confirmed by the fluorescent antibody technique and the enzyme immunoassay using the monoclonal antibodies against CAM-70 strain and Momo strain.

EXAMPLE 3

Modification of a Genome of a Live Attenuated Vaccine Strain:

A recombinant CAM-70 virus which is vaccine virus CAM-70 strain having a part of its H protein replaced by the corresponding part of the H protein of epidemic measles NA strain is prepared in substantially the same manner as mentioned in Example 2, except that the method is modified in the following manner {modified method described in item [II](1) above}.

First, the viral genomic RNA is extracted from the CAM-70 strain, and the cDNA is prepared from the genomic RNA by RT-PCR (reverse transcript-PCR) method. The genes coding for N, P and L proteins are cloned individually from the prepared cDNA by a customary method using primers [hereinbelow, each of the clones are referred to as "pcDNA3.1(−)/N", "pcDNA3.1(−)/P" and "pcDNA3.1(−)/L"]. The clones are amplified in *E. Coli* and stored for use in the subsequent procedure.

In addition to the above, the cDNA derived from the full length viral genomic RNA of CAM-70 strain, in which a part of its H protein gene is replaced by the corresponding part of the H protein gene of NA strain, is cloned by using plasmids pbluescript SK or KS in substantially the same manner as mentioned above, to thereby obtain clone pBluescript/MV. The obtained clone is amplified and stored for use in the subsequent procedure. With respect to the nucleotide sequence replaced in the cDNA for CAM-70 strain, the region consisting of the 526th to 948th nucleotides (total of 423 nucleotides encoding the 176th to 316th amino acids) of the CAM-70 strain H protein gene of SEQ ID NO: 1 is replaced with the corresponding region (the 526th to 948th nucleotides) in the NA strain H protein gene of SEQ ID NO: 9.

The above-mentioned pcDNA3.1(−)/N, pcDNA3.1(−)/P, pcDNA3.1(−)/L and pBluescript/MV are co-transfected to MRC-5 cells which have already been transfected with recMVA (FEBS Letter, vol. 371, no. 1, pp. 9–12, 1995), and then, the transfected cells are cultured at 37° C. to thereby obtain a recombinant virus. The antigenicity of the recombinant virus is confirmed by the fluorescent antibody technique and the enzyme immunoassay using the monoclonal antibodies against CAM-70 strain and NA strain. The antigenicity of the recombinant virus is on the same level as that of the epidemic strains, and since the recombinant virus is attenuated, it can be used as an active component for a live attenuated measles vaccine.

EXAMPLE 4

Preparation of an Active Component for a Gene Vaccine:

A non-proliferating recombinant adenovirus is prepared in accordance with the method of Saito et al. described in item [II](2) above. With respect to the gene which is inserted into the non-proliferating viral genome (i.e., cassette cosmid pAdex1), use is made of a ligation product of the cDNAs for the H protein gene and F protein gene of NA strain respectively shown in SEQ ID NO: 9 and SEQ ID NO: 19. The two cDNAs are ligated in the order of F protein-H protein in the direction from the 5' end to the 3' end, so that the F protein and the H protein are expressed in the form of an F-H fusion protein. The ligated cDNA is inserted into the E1A·E1B deletion site of the cassette cosmid pAdex1 cleaved with a restriction enzyme SwaI, to thereby obtain pAdex1/FH.

With respect to the cDNAs for the H protein gene and the F protein gene, the cDNAs are prepared from the NA strain genomic RNA by RT-PCR method using primers which correspond to the respective genes. Further, pAdex1/FH is packaged into a λphage so as to be amplified in E. coli, and stored for use in the subsequent procedure.

Subsequently, the DNA-TPC (viral DNA-Terminal Protein Complex) of the parent adenovirus strain is extracted and purified from the infected cells by CsCl ultracentrifugation method, and the purified DNA-TPC is digested with restriction enzyme Eco T22I to thereby obtain the digestion product DNA-TPC/Eco T22I. Then, using calcium phosphate method, the above-obtained pAdex1/FH and DNA-TPC/Eco T22I are co-transfected to the cultured cells of 293 cell line, thereby obtaining transfectants, followed by culturing the transfectants at 37° C. for 18 hours to advance the homologous recombination between the DNAs. As a result of the homologous recombination, a non-proliferating recombinant adenovirus having both the H and F proteins of NA strain is obtained from the cultured transfectants.

The fluorescent antibody technique using monoclonal antibodies against each of the H and F proteins is conducted to select the recombinant virus and confirm its proliferation in the transfected cells of 293 cell line (which are the permissive host cells for the adenovirus).

EXAMPLE 5

Preparation of a Diagnostic Reagent:

The peptides having the following amino acid sequences are synthesized using a peptide synthesizer (Model ABI 432A manufactured and sold by Perkin-Elmer Cetus Co., Ltd., U.S.A.): "Leu Glu Ala Arg Ala Thr Asn", "Asn Leu Ser Ser Lys Gly Ser", "Glu Gln Ser Val Ser Asn" and "His Arg Glu Asp Ser Ile Thr". Each of the synthesized peptides is used as an antigen for recognizing and identifying the infection with the epidemic strains.

INDUSTRIAL APPLICABILITY

By the use of the measles virus mutant antigen or the gene coding for the same of the present invention, it has become possible to provide efficiently and economically a live attenuated measles vaccine or gene vaccine which is adapted for an epidemic strain of measles virus, and a diagnostic reagent capable of accurately detecting infections with an epidemic strain of measles virus.

---

What is claimed is:

1. A measles virus mutant antigen consisting of
   a measles virus mutant H protein antigen, wherein said measles virus mutant H protein antigen is at least one member selected from the group consisting of the following amino acid sequences (a) to (c)
   (a) an amino acid sequence of SEQ ID NO: 10;
   (b) an amino acid sequence of SEQ ID NO: 3 or SEQ ID NO: 11; and
   (c) an amino acid sequence of SEQ ID NO: 4 or SEQ ID NO: 12.

2. A recombinant measles virus mutant antigen obtained by replacing a part of the H protein of CAM-70 strain shown in SEQ ID NO: 2 by a corresponding part of the H protein of NA strain shown in SEQ ID NO: 10.

3. The recombinant measles virus antigen according to claim 2, wherein the 176th to 316th amino acids of SEQ ID NO: 2 are replaced by the amino acid sequence of SEQ ID NO: 12.

* * * * *